(12) United States Patent
Peri et al.

(10) Patent No.: US 6,864,239 B2
(45) Date of Patent: Mar. 8, 2005

(54) METHODS AND COMPOUNDS FOR PREVENTION AND TREATMENT OF ELEVATED INTRAOCULAR PRESSURE AND RELATED CONDITIONS

(75) Inventors: Krishna G. Peri, Montréal (CA); Serge Moffett, St-Laurent (CA); Daniel Abran, Vaudreuil-Dorion (CA)

(73) Assignee: Theratechnologies Inc., St. Laurent (CA)

( * ) Notice: Subject to any disclaimer, the term of this patent is extended or adjusted under 35 U.S.C. 154(b) by 0 days.

(21) Appl. No.: 10/401,397

(22) Filed: Mar. 27, 2003

(65) Prior Publication Data

US 2003/0212001 A1 Nov. 13, 2003

Related U.S. Application Data

(60) Provisional application No. 60/367,513, filed on Mar. 27, 2002.

(51) Int. Cl.$^7$ .............................................. A61K 38/00
(52) U.S. Cl. ............................................ 514/16; 514/2
(58) Field of Search ....................................... 514/16, 2

(56) References Cited

PUBLICATIONS

Dong et al., (2001) "A Diverse Family of GPCRs Expressed in Specific Subsets of Nociceptive Sensory Neurons", *Cell*, 106:619–632.

Gonzalez et al., (2000) "Characterization of Gene Expression in Human Trabecular Meshwork Using Single–Pass Sequencing of 1060 Clones", *Invest. Ophtalmol. Vis. Sci.*, 41:3678–3693.

(2000) GenBank Accession No. BE439409; HTM1–025F1 Homo Sapiens cDNA, mRNA seqeunce.

*Primary Examiner*—Christopher R. Tate
*Assistant Examiner*—Jennifer Ione Harle
(74) *Attorney, Agent, or Firm*—Darby & Darby

(57) ABSTRACT

A GPCR-like protein is described, as well as inhibitory/antagonistic compounds and compositions comprising such inhibitors/antagonists of the protein. Such compounds may be used for treating elevated intraocular pressure and conditions associated with elevated intraocular pressure, such as glaucoma.

29 Claims, 6 Drawing Sheets

FIGURE 1B (SEQ ID NO:1)

```
1    ATGGATTCAA CCATCCCAGT CTTGGGTACA GAACTGACAC CAATCAACGG
51   ACGTGAGGAG ACTCCTTGCT ACAAGCAGAC CCTGAGCTTC ACGGGGCTGA
101  CGTGCATCGT TTCCCTTGTC GCGCTGACAG GAGACGCGGT TGTGCTCTGG
151  CTCCTGGGCT GCCGCATGCG CAGGAACGCT GTCTCCATCT ACATCCTCAA
201  CCTGGTCGCG GCCGACTTCC TCTTCCTTAG CGGCCACATT ATATGTTCGC
251  CGTTACGCCT CATCAATATC CGCCATCCCA TCTCCAAAAT CCTCAGTCCT
301  GTGATGACCT TTCCCTACTT TATAGGCCTA AGCATGCTGA GCGCCATCAG
351  CACCGAGCGC TGCCTGTCCA TCCTGTGGCC CATCTGGTAC CACTGCCGCC
401  GCCCCAGATA CCTGTCATCG GTCATGTGTG TCCTGCTCTG GGCCCTGTCC
451  CTGCTGCGGA GTATCCTGGA GTGGATGTTC TGTGACTTCC TGTTTAGTGG
501  TGCTGATTCT GTTTGGTGTG AAACGTCAGA TTTCATTACA ATCGCGTGGC
551  TGGTTTTTTT ATGTGTGGTT CTCTGTGGGT CCAGCCTGGT CCTGCTGGTC
601  AGGATTCTCT GTGGATCCCG GAAGATGCCG CTGACCAGGC TGTACGTGAC
651  CATCCTCCTC ACAGTGCTGG TCTTCCTCCT CTGTGGCCTG CCCTTTGGCA
701  TTCAGTGGGC CCTGTTTTCC AGGATCCACC TGGATTGGAA AGTCTTATTT
751  TGTCATGTGC ATCTAGTTTC CATTTTCCTG TCCGCTCTTA ACAGCAGTGC
801  CAACCCCATC ATTTACTTCT TCGTGGGCTC CTTTAGGCAG CGTCAAAATA
851  GGCAGAACCT GAAGCTGGTT CTCCAGAGGG CTCTGCAGGA CACGCCTGAG
901  GTGGATGAAG GTGGAGGGTG GCTTCCTCAG GAAACCCTGG AGCTGTCGGG
951  AAGCAGATTG GAGCAGTAA
```

FIGURE 1C (SEQ ID NO:2)

```
1    MDSTIPVLGTELTPINGREETPCYKQTLSFTGLTCIVSLVALTGNAVVLWLLGCRMRRNA
61   VSIYILNLVAADFLFLSGHIICSPLRLINIRHPISKILSPVMTFPYFIGLSMLSAISTER
121  CLSILWPIWYHCRRPRYLSSVMCVLLWALSLLRSILEWMFCDFLFSGANSVWCETSDFIT
181  IAWLVFLCVVLCGSSLVLLVRILCGSRKMPLTRLYVTILLTVLVFLLCGLPFGIQWALFS
241  RIHLDWKVLFCHVHLVSIFLSALNSSANPIIYFFVGSFRQRQNRQNLKLVLQRALQDTPE
301  VDEGGGWLPQETLELSGSRLEQ
```

METHODS AND COMPOUNDS FOR PREVENTION AND TREATMENT OF ELEVATED INTRAOCULAR PRESSURE AND RELATED CONDITIONS

CROSS-REFERENCE TO RELATED APPLICATION

This application claims the benefit of U.S. provisional application No. 60/367,513 filed Mar. 27, 2002.

FIELD OF THE INVENTION

The invention relates to methods and compounds for the prevention and/or treatment of ocular hypertension or elevated intraocular pressure, and related conditions such as glaucoma.

BACKGROUND OF THE INVENTION

Glaucoma and Intraocular Pressure

Glaucoma is characterized by optic nerve head excavation which can lead to loss of peripheral vision and sometimes loss of central vision. Glaucoma is the second leading cause of vision loss worldwide; an estimated 66.8 million people will have primary glaucoma and 6.7 million will be bilaterally blind due to this disorder. In the United States, glaucoma is the second leading cause of permanent blindness and the leading cause among African Americans. While glaucoma is treatable and vision loss can be prevented, once vision loss occurs it is irreversible. Elevated intraocular pressure (IOP) is a major risk factor for the development of glaucoma, but it is not found in all patients with the disease (Sommer, A. et al., *Arch. Ophthalmol.* 109: 1090–1095 (1991)). Glaucoma associated with elevated IOP is divided into three major categories: open angle, closed angle and developmental. Each of these categories is further divided into primary and secondary forms, and by the age of onset. Drugs that lower IOP, such as latanoprost, unoprost, timolol which target prostaglandin $F_{2\alpha}$ and $\beta_2$ adrenergic receptors are being currently used to prevent and delay ocular degeneration in glaucomatous patients.

There is therefore a continued need to identify and characterize targets and in turn products for the prevention and treatment of ocular disorders, such as glaucoma.

SUMMARY OF THE INVENTION

The invention relates to R-14 nucleic acids and polypeptides and compounds capable of lowering intraocular pressure and uses thereof.

Accordingly, in an aspect, the invention provides a substantially pure peptide compound of Formula I:

$$Z_1\text{-}X_1\text{-}X_2\text{-}X_3\text{-}X_4\text{-}X_5\text{-}X_6\text{-}X_7\text{-}X_8\text{-}Z_2 \qquad \text{I}$$

wherein:

$X_1$ is selected from the group consisting of Phe, His, Ile and related amino acids;

$X_2$ is selected from the group consisting of Ser, Ile, Phe and related amino acids $X_3$ is selected from the group consisting of Leu, Ile, Asp and related amino acids $X_4$ is selected from the group consisting of Thr, Cys, Ser and related amino acids possessing side chains containing sulfhydryl, hydroxyl or H-bond forming groups;

$X_5$ is selected from the group consisting of Gln, Ser, Thr and related amino acids;

$X_6$ is selected from the group consisting of Lys, Pro, Glu and related amino acids;

$X_7$ is selected from the group consisting of Tyr, Leu, Cys and related amino acids;

$X_8$ is selected from the group consisting of Cys, Arg, Trp and related amino acids;

$Z_1$ is an N-terminal group of the formula $H_2N$—, RHN— or, RRN—;

$Z_2$ is a C-terminal group of the formula —C(O)OH, —C(O)R, —C(O)OR, —C(O)NHR, —C(O)NRR;

R at each occurrence is independently selected from ($C_1$–$C_6$) alkyl, ($C_1$–$C_6$) alkenyl, ($C_1$–$C_6$) alkynyl, substituted ($C_1$–$C_6$) alkyl, substituted ($C_1$–$C_6$) alkenyl, or substituted ($C_1$–$C_6$) alkynyl; and "—" is a covalent linkage.

The invention further provides a substantially pure synthetic peptide compound or recombinant peptide compound, said compound having a domain of Formula II:

$$\text{-}X_1\text{-}X_2\text{-}X_3\text{-}X_4\text{-}X_5\text{-}X_6\text{-}X_7\text{-}X_8 \qquad \text{II}$$

wherein $X_1$, $X_2$, $X_3$, $X_4$, $X_5$, $X_6$, $X_7$, $X_8$ and "—" are as defined above.

In embodiments, the compound is selected from the group consisting of: FSLTQKYC; HIICSPLR; and IFDSTECW. In embodiments, the domain is selected from the group consisting of: FSLTQKYC; HIICSPLR; and IFDSTECW.

The invention further provides a method of lowering intraocular pressure in a subject, said method comprising administering to said subject an effective amount of the above-mentioned compound.

The invention further provides a method of treating in a subject a condition associated with elevated intraocular pressure, said method comprising administering to said subject an effective amount of the above-mentioned compound.

In embodiments, the methods comprise administering said compound to an eye of said subject.

The invention further provides a pharmaceutical composition comprising the above-mentioned compound in admixture with a pharmaceutically acceptable carrier. In an embodiment, the composition is formulated for administration to an eye of a subject.

The invention further provides a commercial package comprising the above-mentioned compound together with instructions for its use. In embodiments, the use is selected from the group consisting of: (a) lowering intraocular pressure in a subject; and (b) treating a condition associated with elevated intraocular pressure.

The invention further provides an isolated nucleic acid comprising a sequence that encodes the above-mentioned domain. The invention further provides a vector comprising the nucleic acid operably-linked to a transcriptional regulatory element. The invention further provides a host cell comprising the vector.

The invention further provides a method of producing the above-mentioned peptide compound, comprising culturing the above-mentioned host cell under conditions permitting expression of the peptide compound.

The invention further provides an isolated nucleic acid comprising a sequence that encodes a polypeptide comprising at least 278 amino acids of SEQ ID NO:2. In an embodiment, the polypeptide comprises SEQ ID NO:2. In an embodiment, the nucleic acid comprises SEQ ID NO:1 or a sequence substantially identical thereto.

The invention further provides a substantially pure polypeptide comprising at least 278, consecutive amino acids of SEQ ID NO:2. In a further embodiment, the polypeptide comprises SEQ ID NO:2.

The invention further provides a vector comprising the above-mentioned nucleic acid operably linked to a transcriptional regulatory element. The invention further provides a host cell comprising the above-mentioned vector.

The invention further provides a method of producing the above-mentioned polypeptide, comprising culturing the above-mentioned host cell under conditions permitting the expression of the polypeptide.

The invention further provides a method for identifying a compound for: (i) lowering intraocular pressure in a subject; (ii) treating a condition associated with elevated intraocular pressure; or (iii) both (i) and (ii); said method comprising: (a) providing a cell expressing an R-14; (b) contacting the cell with a test compound; and determining whether R-14 activity is decreased in the presence of said test compound, said decrease in activity being an indication that said compound may be useful for: (i) lowering intraocular pressure in a subject; (ii) treating a condition associated with elevated intraocular pressure; or (iii) both (i) and (ii). In an embodiment, said decrease in activity is an indication that said compound is an R-14 antagonist. In an embodiment, R-14 comprises a polypeptide comprising SEQ ID NO:2, an active fragment thereof, or a sequence substantially identical thereto.

The invention further provides a use of the above-mentioned compound for: (a) lowering intraocular pressure in a subject; (b) treating a condition associated with elevated intraocular pressure; or (c) both (a) and (b).

The invention further provides a use of the above-mentioned compound or the above-mentioned composition for the preparation of a medicament. In an embodiment, the medicament is for: (a) lowering intraocular pressure in a subject; (b) treating a condition associated with elevated intraocular pressure; or (c) both (a) and (b).

In an embodiment, the above-mentioned condition is glaucoma.

In an embodiment, the above-mentioned subject is a mammal, in a further embodiment, a human.

In further embodiments, $Z_1$ is selected from the group consisting of a proton, a sequence of 1–3 amino acids, or a blocking group such as a carbamate group, an acyl group composed of a hydrophobic moiety such as cyclohexyl, phenyl, benzyl, short chain linear and branched alkyl groups of 1–8 carbons. In further embodiments $Z_2$ is selected from the group consisting of proton, $NH_2$, 1–3 amino acids as well as arylalkyl amines such as benzylamine, phenylethylamine, phenylpropylamine, and aliphatic amines possessing short chain linear and branched alkyl groups of 1 to 8 carbons.

In another aspect, the invention provides a method for formulating a medicament, the method comprising admixing a compound of the invention with a pharmaceutically acceptable carrier.

In another aspect, the invention provides a method of lowering intraocular pressure in a subject, the method comprising inhibiting expression and/or activity of an R-14 protein in the subject. In an embodiment, the R-14 protein comprises a polypeptide selected from the group consisting of:

(a) the polypeptide of SEQ ID. NO. 2; and
(b) a polypeptide encoded by a first nucleic acid that is substantially identical to a second nucleic acid capable of encoding the polypeptide of SEQ ID NO. 2. In an embodiment, the second nucleic acid is as set forth in SEQ ID NO. 1.

In an embodiment, the above-noted method comprises administering to the subject an effective amount of an agent capable of modulating R-14 activity. In an embodiment, the agent is a compound of the invention. In a further embodiment, the method comprises administering to the subject a therapeutically-effective dose of the above-mentioned composition. In an embodiment, the dose is of about 0.001 mg to of about 100 mg.

The invention further provides a method of lowering intraocular pressure in a subject, the method comprising administering to the subject an effective amount of a compound of the invention. In an embodiment, the method comprises administering to the subject a therapeutically-effective dose of the above-mentioned composition. In an embodiment, the dose is of about 0.001 mg to of about 100 mg.

The invention further provides a method of preventing or treating in a subject a condition associated with elevated intraocular pressure, the method comprising inhibiting expression and/or activity of an R-14 protein in the subject. In an embodiment, the R-14 protein comprises a polypeptide selected from the group consisting of:

(a) the polypeptide of SEQ ID NO. 2; and
(b) a polypeptide encoded by a first nucleic acid that is substantially identical to a second nucleic acid capable of encoding the polypeptide of SEQ ID NO. 2. In an embodiment, the second nucleic acid is as set forth in SEQ ID NO. 1.

In an embodiment, the method comprises administering to the subject an effective amount of an agent capable of modulating R-14 activity. In an embodiment, the agent is a compound of the invention. In a further embodiment, the method comprises administering to the subject a therapeutically-effective dose of the above-mentioned composition. In an embodiment, the dose is of about 0.001 mg to of about 100 mg.

The invention further provides a method of preventing or treating in a subject a condition associated with elevated intraocular pressure, the method comprising administering to the subject an effective amount of a compound of the invention. In a further embodiment, the method comprises administering to the subject a therapeutically-effective dose of the above-mentioned composition. In an embodiment, the dose is of about 0.001 mg to of about 100 mg.

The invention further provides a commercial package comprising an agent capable of modulating R-14 activity together with instructions for:
(a) lowering intraocular pressure in a subject;
(b) preventing or treating a condition associated with elevated intraocular pressure; or
(c) both (a) and (b).

In an embodiment, the R-14 protein comprises a polypeptide selected from the group consisting of:
(i) the polypeptide of SEQ ID NO. 2; and
(ii) a polypeptide encoded by a first nucleic acid that is substantially identical to a second nucleic acid capable of encoding the polypeptide of SEQ ID NO. 2.

The invention further provides a method for identifying and/or characterizing a compound for lowering intraocular pressure, the method comprising assaying the activity of an R-14 in the presence of a test compound, to identify a compound that acts as an R-14 antagonist, wherein antagonist activity is indicative that the test compound may be useful for lowering intraocular pressure.

The invention further provides a method for identifying and/or characterizing a compound for lowering intraocular pressure, the method comprising:

(a) contacting a test compound with a host cell expressing a polypeptide selected from the group consisting of:
  (i) the polypeptide of SEQ ID NO. 2; and
  (ii) a polypeptide encoded by a first nucleic acid that is substantially identical to a second nucleic acid capable of encoding the polypeptide of SEQ ID NO. 2; and
(b) assaying activity of an R-14 in the presence of the test compound, to identify a compound that acts as an R-14 antagonist, wherein antagonist activity is indicative that the test compound may be useful for lowering intraocular pressure. In an embodiment, the compound may be used for the prevention and/or treatment of a condition associated with intraocular pressure.

In an embodiment, the above-mentioned subject is a mammal, in a further embodiment, a human.

In an embodiment, the above-mentioned condition is glaucoma.

Figure 1A:
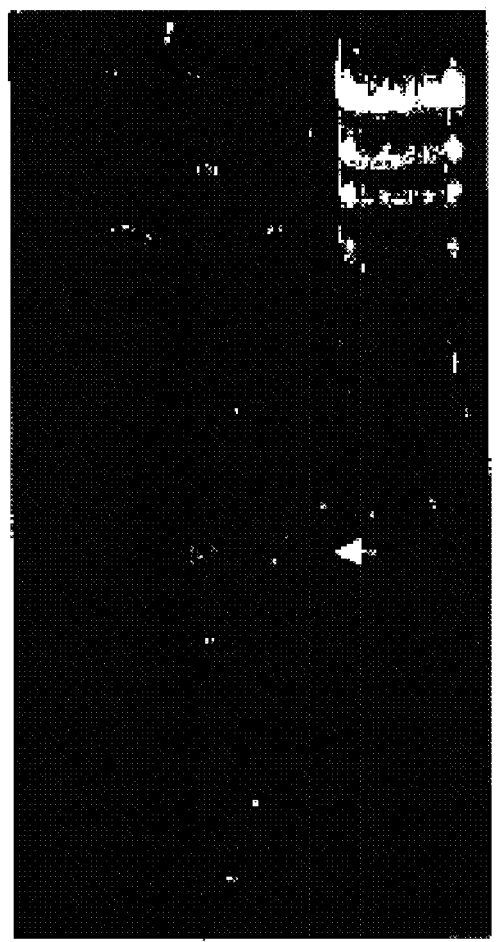
FIG. 1: (A) Agarose gel electrophoretic resolution of ~960 bp product (arrow) obtained by PCR amplification as described in Example 1. −Bac: No plasmid DNA; +Bac: contains plasmid DNA (0.1 $\mu$g); MW std: $\lambda$ Hind III digest. (B). The nucleotide sequence of the R-14 reading frame (SEQ ID NO:1). (C) R-14 polypeptide sequence (SEQ ID NO:2).
Figure 2:
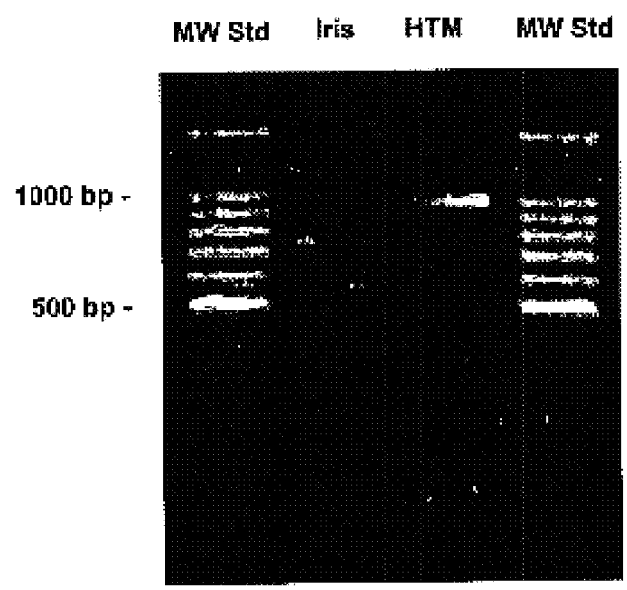
FIG. 2: Agarose gel electrophoretic analysis of RT-PCR products for analysis of R-14 expression as described in Example 2. Iris: sample derived from Iris tissue; HTM: sample derived from human trabecular meshwork tissue.

Other objects, advantages and features of the present invention will become more apparent upon reading of the following non-restrictive description of preferred embodiments with reference to the accompanying drawings, which is exemplary and should not be interpreted as limiting the scope of the present invention.

DETAILED DESCRIPTION OF THE INVENTION

Identification of Novel GPCRs

Use of low stringency hybridization, differential display, microarrays, subtractive hybridization and other techniques followed by cloning of differentially expressed genes in tissues have disclosed several new cDNAs which could potentially code for new G protein-coupled receptors. Following the elucidation of the draft sequence of the human genome (Venter, J C. et al., *Science*. 291: 1304–1351 (2001); International Human Genome Sequencing Consortium. *Nature*. 409: 860–921 (2001)), many GPCR-like sequences have been identified based on their canonical seven transmembrane topology as well as conserved protein motifs (Howard, D A et al., 2001. *Trends Pharmacol. Sci.* 22(3): 132–140). These unique GPCR-like sequences number ~1000 of which nonolfactory GPCR sequences are estimated to be ~616.

Gonzalez et al. (Gonzalez, P. et al., 2000. *Invest. Ophthalmol. Vis. Sci.* 41: 3678–3673), carried out single pass sequencing of 1060 cDNA clones isolated from human trabecular meshwork, including a sequence having homology to MAS-related G-protein coupled receptor (denoted as HTMI-0025, and corresponding to sequences Hs11_9464 and Hs11_24438 found in the human chromosome 11 working draft sequence).

Dong et al. (Dong, X. et al. 2001. *Cell* 106:619–632) cloned several mas-related cDNAs from mouse embryos lacking neurogenin gene, with subsequent searching among human genome sequences revealing four related genes (called Hs_mrgX1–4).

When the physiological ligand(s) of a GPCR is not known, then it is termed an orphan GPCR. In order to find ligands of these orphan GCPRs, random libraries containing natural peptides isolated from the tissues or those containing small molecules produced by combinatorial chemistry or from natural sources are screened in cell-based and in vitro assays. Selective modulators of the orphan GPCR can be used to assess its function in physiology and pathophysiology using appropriate animal models. Finding a function of the orphan GPCR is a first step towards analyzing its potential as a new drug target.

The studies described herein relate to a novel GPCR protein expressed in trabecular meshwork, nucleic acids capable of encoding it, and peptide compounds capable of modulating phenomena in ocular tissue, notably intraocular pressure.

In one aspect, the invention provides an isolated a GPCR-like reading frame, which is capable of expressing mRNA and protein, and is associated with a role in ocular outflow in animals. The invention further provides three antagonists of the GPCR which could be used for lowering intraocular pressure, and thus for prevention/treatment of disorders associated with elevated intraocular pressure, such as glaucoma and related conditions.

As described herein, applicants have cloned a genomic DNA fragment of 0.97 Kb in length from a BAC clone and have shown that it contained a single exon encoding a 322 amino acid long protein. This protein is termed as R-14. From in silico analysis, R-14 appears to be an integral membrane protein containing seven prominent transmembrane domains and many protein motifs of G protein-coupled receptors. By employing RT-PCR, R-14 mRNA is shown to be expressed in human trabecular meshwork, but not in another ocular tissue, iris. R-14 reading frame was cloned into mammalian expression vectors and transiently as well as stably expressed in HEK293 cells. Using these cells, a protein of 40 kDa was identified to be encoded by the recombinant R-14 gene. Furthermore, using selective peptidic ligands, applicants have shown that inhibition of R-14 receptor resulted in reduction of basal cyclic AMP synthesis, but not basal phosphoinositide levels, in porcine trabecular meshwork and most importantly, reduction of basal intraocular pressure in rabbits, adult pig eyes and anesthetized piglets. Based on this information, R-14 receptor is identified as a useful target for screening for ocular hypotensive drugs, which may be useful for treatment of conditions associated with elevated intraocular pressure such as glaucoma and related conditions.

Furthermore, compositions containing selective inhibitors of R-14 receptor are described which could be potentially used as ocular hypotensive drugs and glaucoma therapeutics or as lead compounds towards development of such drugs. Bioassays in which host cells (e.g. mammalian cells) containing recombinantly expressed R-14 are described which can be used to screen chemical compound libraries to identify lead compounds for providing R-14 ligands which in turn can be optimized into ocular hypotensive drugs and glaucoma therapeutics.

Definitions

For convenience, the meaning of certain terms and phrases employed in the specification, examples, and appended claims are provided below.

The term "agonist", as used herein, is meant to refer to an agent that potentiates at least one aspect of R-14 bioactivity. R-14 bioactivity can be increased for example, by stimulating the wild-type activity and signal transduction, or enable the wild type R-14 protein to interact more efficiently with other proteins which are involved in signal transduction cascade.

"Antagonist" as used herein is meant to refer to an agent that inhibits at least one R-14 bioactivity. An R-14 antagonist can be a compound which inhibits or decreases the interaction between a R-14 protein and another molecule, or decreases the synthesis and expression of R-14 polypeptide or inhibits the bioactivity of R-14 molecule. The antagonist can be a nucleic acid molecule, such as a dominant negative form of R-14, an R-14 antisense molecule, a ribozyme capable of specifically interacting with R-14 mRNA, or molecules which bind to a R-14 polypeptide e.g. peptides, antibodies, small molecules.

An "agent capable of modulating R-14 activity" refers to any compound which when introduced into a system comprising an R-14 protein, is capable of altering at least one aspect of R-14 activity or function. Such an agent may be a ligand of an R-14 protein, in further embodiments an agonist or antagonist as defined above. Such an agent may act directly on an R-14 protein or indirectly by modulating a process or activity which subsequently results in the modulation of R-14 activity. In certain systems (e.g. in vivo), such an agent may be a prodrug which is metabolised to an active form at or prior to its arrival at the site of action. Examples of R-14 activity are noted below.

The term "amino acid" as used herein includes both L and D isomers of the naturally occurring amino acids (Table 1) as well as other nonproteinaceous amino acids used in peptide chemistry to prepare synthetic analogs of peptides. Examples of naturally-occurring amino acids are glycine, alanine, valine, leucine, isoleucine, serine, threonine, etc. whereas nonproteinaceous amino acids are norleucine, norvaline, cyclohexyl alanine, biphenyl alanine, homophenyl alanine, naphthyl alanine, pyridyl alanine, phenyl alanines substituted at the ortho, para and meta positions with alkoxy, halogen or nitro groups etc. These compounds are known to persons versed in the art of peptide chemistry.

TABLE 1

Common notations of amino acids (L-amino acids by capital letters and D-amino acids by small letters are represented by convention; glycine does not have L/D forms)

| Full Name | 3-Letter Code | 1-Letter Code |
|---|---|---|
| Aspartic Acid | Asp | D/d |
| Glutamic Acid | Glu | E/e |
| Lysine | Lys | K/k |
| Arginine | Arg | R/r |
| Histidine | His | H/h |
| Tyrosine | Tyr | Y/y |
| Cysteine | Cys | C/c |
| Asparagine | Asn | N/n |
| Glutamine | Gln | Q/q |
| Serine | Ser | S/s |
| Threonine | Thr | T/t |
| Glycine | Gly | G |
| Alanine | Ala | A/a |
| Valine | Val | V/v |
| Leucine | Leu | L/l |
| Isoleucine | Ile | I/I |
| Methionine | Met | M/m |
| Proline | Pro | P/p |
| Phenylalanine | Phe | F/f |
| Tryptophan | Trp | W/w |

"Biological activity" or "bioactivity" or "activity" or "biological function", which are used interchangeably, for the purposes herein means a function that is directly or indirectly performed by an R-14 polypeptide, or by any fragment thereof. In this instance, biological activities of R-14 include binding to another molecule, interaction with other proteins, alterations in signal transduction such as guanine nucleotide binding by $G_\alpha$ proteins, calcium fluxes, cAMP synthesis, inositol phosphate synthesis, internalization of R-14 polypeptide, association with other intracellular proteins or coated pits in cell membrane, alterations in intraocular pressure, elevation of aqueous humor transit through the Schlemm's canal etc.

"Cells", "host cells" or "recombinant host cells" are terms used interchangeably herein. It is understood that such terms refer not only to the particular cell but to all its progeny. Also within the scope of the term are cells of mammalian (e.g. human), amphibian, fungal (e.g. yeast), and bacterial (e.g. *E. coli*) origin.

A "fusion polypeptide" can be represented by the general formula X-(R-14)-Y, wherein R-14 represents a portion of the polypeptide which is derived from a R-14 polypeptide, and X and Y are amino acid sequences and are independently present or absent in the fusion peptide.

As used herein, the term "nucleic acid" refers to polynucleotides or oligonucleotides such as deoxyribonucleic acid (DNA), and, where appropriate, ribonucleic acid (RNA).

The terms "protein" and "polypeptide" are used interchangeably herein when referring to a gene product.

The term "R-14 nucleic acid" refers to a nucleic acid capable of encoding an R-14 protein, such as nucleic acids having SEQ ID NO. 1, as well as fragments thereof, and sequences substantially identical thereto.

The terms "R-14 polypeptide" and "R-14 protein" are intended to encompass polypeptides comprising the amino acid sequence shown as SEQ ID NO:2 or fragments, variants and homologs thereof.

"Homology" and "homologous" refers to sequence similarity between two peptides or two nucleic acid molecules.

Homology can be determined by comparing each position in the aligned sequences. A degree of homology between nucleic acid or between amino acid sequences is a function of the number of identical or matching nucleotides or amino acids at positions shared by the sequences. An "unrelated" or "non-homologous" sequence shares less than 40% identity, though preferably less than about 25% identity, with SEQ ID Nos:1 or 2 of the present invention.

Substantially complementary nucleic acids are nucleic acids in which the "complement" of one molecule is substantially identical to the other molecule. Two nucleic acid or protein sequences are considered "substantially identical" if, when optimally aligned, they share at least about 70% sequence identity. In alternative embodiments, sequence identity may for example be at least 75%, at least 80%, at least 85%, at least 90%, or at least 95%. Optimal alignment of sequences for comparisons of identity may be conducted using a variety of algorithms, such as the local homology algorithm of Smith and Waterman,1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403–10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with, a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915–10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

The term "interact" as used herein is meant to include detectable relationships or associations (e.g. biochemical interactions) between molecules, such as interaction between protein-protein, protein-nucleic acid, nucleic acid-nucleic acid, and protein-small molecule or nucleic acid-small molecule in nature.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "peptide" is intended to mean a linear polymer containing at least 2 amino acids to a maximum of 50 amino acids. In further embodiments the peptide contains 2 to 25 amino acids, 2 to 20 amino acids, 2 to 15 amino acids, 2 to 10 amino acids or 8 amino acids. The amino acids can be naturally-occuring or synthetically-derived molecules. Examples of such molecules are L-amino acids, D-amino acids, and synthetic analogues of natural amino acids including but not limited to nonproteinaceous amino acids.

The term "peptidomimetic" refers to a molecule that mimics the structural and/or functional features of a peptide. Persons skilled in the art use variety of methods to derive peptidomimetics of a peptide: substitutions of individual amino acids with synthetic chemical entities, nonproteinaceous amino acid analogues, deletions, additions of amino acids, replacing one or more of amino acids in the peptide with scaffolds such as beta turn mimetics, or with known pharmacophores. A description of the general methods are given in *Peptidomimetic protocols* (*Methods in molecular medicine* Vol. 23) W. M. Kazmierski (ed.), Humana Press and *Advances in Amino Acid Mimetics and Peptidomimetics*, Vols. 1 & 2 A. Abell (Ed).

The term "recombinant protein" refers to a polypeptide of the present invention which is produced by recombinant DNA techniques, wherein generally, DNA encoding a R-14 polypeptide is inserted into a suitable expression vector which is in turn used to transform a host cell to produce the heterologous protein. "Recombinant" means that something has been recombined, so that when made in reference to a nucleic acid construct the term refers to a molecule that is comprised of nucleic acid sequences that are joined together or produced by means of molecular biological techniques.

The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny or cell or genome with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors".

The recombinant expression vector of the present invention can be constructed by standard techniques known to one of ordinary skill in the art and found, for example, in Sambrook et al. (1989) in Molecular Cloning: A Laboratory Manual. A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation and selection in bacteria and host cells. In addition, the vectors of the present invention may comprise a sequence of nucleotides for one or more restriction endonuclease sites. Coding sequences such as for selectable markers and reporter genes are well known to persons skilled in the art.

A recombinant expression vector comprising a nucleic acid sequence of the present invention may be introduced into a host cell, which may include a living cell capable of expressing the protein coding region from the defined recombinant expression vector. The living cell may include both a cultured cell and a cell within a living organism. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (Molecular Cloning: A Laboratory Manual, 2nd Edition, Cold Spring Harbor Laboratory press (1989)), and other laboratory manuals. Methods for introducing DNA into mammalian cells in vivo are also known, and may be used to deliver the vector DNA of the invention to a subject for gene therapy for lowering intraocular pressure and/or for treating associated conditions, such as glaucoma.

"Transcriptional regulatory sequence/element" is a generic term that refers to DNA sequences, such as initiation and termination signals, enhancers, and promoters, splicing signals, polyadenylation signals which induce or control transcription of protein coding sequences with which they are operably linked. In the present invention, transcription of one of the R-14 genes is under the control of a promoter sequence which controls the expression of the recombinant gene in a cell-type. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous.

As used herein, the term "transfection" means the introduction of a nucleic acid, e.g., via an expression vector, into a recipient cell by nucleic acid-mediated gene transfer.

A cell (e.g. a host cell or indicator cell), tissue, organ, or organism into which has been introduced a foreign nucleic acid (e.g. exogenous or heterologous DNA [e.g. a DNA construct]), is considered "transformed", "transfected", or "transgenic". A transgenic or transformed cell or organism also includes progeny of the cell or organism and progeny produced from a breeding program employing a transgenic organism as a parent and exhibiting an altered phenotype resulting from the presence of a recombinant nucleic acid construct. A transgenic organism is therefore an organism that has been transformed with a heterologous nucleic acid, or the progeny of such an organism that includes the transgene. The introduced DNA may be integrated into chromosomal DNA of the cell's genome, or alternatively may be maintained episomally (e.g. on a plasmid). Methods of transfection are well known in the art (Sambrook et al., 1989, supra; Ausubel et al., 1994 supra).

For stable transfection of mammalian cells, it is known that, depending upon the expression vector and transfection technique used, only a small fraction of cells may integrate the foreign DNA into their genome. In order to identify and select these integrants, a gene that encodes a selectable marker (such as resistance to antibiotics) may be introduced into the host cells along with the gene of interest. As used herein, the term "selectable marker" is used broadly to refer to markers which confer an identifiable trait to the indicator cell. Non-limiting example of selectable markers include markers affecting viability, metabolism, proliferation, morphology and the like. Preferred selectable markers include those that confer resistance to drugs, such as G418, hygromycin and methotrexate. Nucleic acids encoding a selectable marker may be introduced into a host cell on the same vector as that encoding the peptide compound or may be introduced on a separate vector. Cells stably transfected with the introduced nucleic acid may be identified by drug selection (cells that have incorporated the selectable marker gene will survive, while the other cells die).

A compound is "substantially pure" when it is separated from the components that naturally accompany it. Typically, a compound is substantially pure when it is at least 60%, more generally 75% or over 90%, by weight, of the total material in a sample. Thus, for example, a polypeptide that is chemically synthesised or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis, HPLC, etc.

"Small molecule" as used herein, is meant to refer to a composition, which has a molecular weight of less than about 1 kD and most preferably less than about 0.4 kD. Small molecules can be nucleotides, amino acids, peptides, peptidomimetics, carbohydrates, lipids or other organic (carbon containing) molecules. Many pharmaceutical companies have extensive libraries of chemical and/or biological mixtures, often fungal, bacterial, or algal extracts, which can be screened with any of the assays of the invention to identify compounds that modulate an R-14 bioactivity.

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. Typical alkyl groups include, but are not limited to, methyl, ethyl, propyl, isopropyl, butyl, isobutyl, t-butyl, pentyl, isopentyl, hexyl, etc. The alkyl groups can be ($C_1$–$C_6$) alkyl, or, ($C_1$–$C_3$) alkyl. A "substituted alkyl" has substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but that contain at least one double or triple bond respectively. An "alkenyl" is an unsaturated branched, straight chain, or cyclic hydrocarbon radical with at least one carbon-carbon double bond. The radical can be in either the cis or trans conformation about the double bond(s). Typical alkenyl groups include, but are not limited to, ethenyl, propenyl, isopropenyl, butenyl, isobutenyl, tert-butenyl, pentenyl, hexenyl, etc. An "alkynyl" is an unsaturated branched, straight chain, or cyclic hydrocarbon radical with at least one carbon-carbon triple bond. Typical alkynyl groups include, but are not limited to, ethynyl, propynyl, butynyl, isobutynyl, pentynyl, hexynyl, etc.

A "therapeutically effective amount" refers to an amount effective, at dosages and for periods of time necessary, to achieve the desired therapeutic result, such as reduction of intraocular pressure and related disorders such as glaucoma. A therapeutically effective amount of a compound of the invention may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or reducing elevated intraocular pressure and in turn preventing or treating related disorders such as glaucoma. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

R14 Nucleic Acids

As noted above, the present invention is based, in part, on the discovery of a human gene, which encodes a human nucleic acid and encoding a protein referred to as "R-14". In silico analysis showed that R-14 could be an integral membrane protein containing seven prominent hydrophobic domains and many signature motifs of a G protein-coupled receptor. The protein and nucleic acid of R-14 show strong homology to human, mouse and rat MAS-related G protein-coupled receptors by BLASTN and BLASTP analyses. A 10.96 kb subclone of BAC RP11-206c1 (obtained from Sanger Center, UK) was completely sequenced and determined to contain the entire coding region of R-14 (SEQ ID NO:1). The human R-14 coding sequence is 0.966 kb in size and contains no introns. The 966 bp open reading frame (SEQ ID NO:1) encodes a 322 amino acid polypeptide (SEQ ID NO:2). BLASTN analysis of dBEST data base revealed near identity to the EST termed as HTMI-0025F1 (GenBank Acc.: BE439409) and the nucleic acid sequence is identical to HTMI-0025 (Gonzalez, P. et al., supra) with the exception of two nucleotide changes, A to C leading to Gln to Pro at 661158 (NT_009307.3 (Hs11_9464).

The invention provides an isolated R-14 nucleic acid, homologs thereof, and portions thereof. Preferred nucleic acids have a sequence, which is at least about 60%, 65%, 70%, 75%, 80%, 85% and preferably 90% and 95% homologous with a nucleotide sequence of an R-14 gene, e.g., such as a sequence shown in SEQ ID NO. 1. Preferred nucleic acids are vertebrate R-14 nucleic acids. Particularly preferred vertebrate R-14 nucleic acids are mammalian, in an embodiment, human. In one embodiment, the preferred nucleic acid is a cDNA encoding a polypeptide having at least one bioactivity of the subject R-14 polypeptide.

R14 Polypeptides

The present invention features R-14 polypeptides which can be produced in and isolated from, cells or tissues in which the the polypeptide is naturally expressed, or cells in which R-14 polypeptide is expressed using gene transfer of recombinant R1–4 nucleic acids, either as cell-free extracts or purified membrane fractions. Functional forms of the subject polypeptides can be prepared as purified preparations by using a cloned gene as described herein. Preferred R-14 proteins of the invention have an amino acid sequence which is at least about 60%, 65%, 70%, 75, 80%, 85%, 90%, or 95% identical or homologous to the amino acid sequence of SEQ ID NO:2. In a preferred embodiment, an R-14 protein of the present invention is a mammalian R-14 protein. In a particularly preferred embodiment an R-14 protein is set forth as SEQ ID NO:2. It will be understood that certain post-translational modifications, e.g., phosphorylation and the like, can increase the apparent molecular weight of the R-14 protein relative to the unmodified polypeptide chain. Protein isoforms encoded by splice variants of R-14 listed in SEQ ID NO:2 are also within the scope of the present invention. Such isoforms may have additional biological activities from those possessed by the R-14 proteins specified by SEQ ID NO:2.

R14 Polypeptide Fusions, Mutant-Proteins and Homologs Thereof

In one aspect, the invention relates to R-14 polypeptides, either as enriched fractions of cells and tissues, or substantially pure preparations of naturally-occurring or recombinantly-produced or chemically-synthesized polypeptides. An R-14 polypeptide of the invention can comprise a full length protein as set forth in SEQ ID NO:2 or can comprises fusion proteins containing smaller fragments corresponding to one or more particular motifs/domains, or fragments comprising at least about 100, 125, 150, 175, 200, 225, 250, 275, 300 amino acids in length. The subject R-14 protein also includes within its scope modified proteins, e.g. proteins in which specific mutations prevent post-translational modification, such as glycosylation, myristylation, palmitylation and phosphorylation of the protein, or which mutations prevent or enhance interaction of the R-14 mutant protein with agonists, antagonists or intracellular proteins involved in signal transduction.

In further embodiments, R-14 polypeptides of the invention may comprise a fragment of the polypeptide of SEQ ID NO:2, as defined by a minimum number of consecutive amino acids thereof. Accordingly, in embodiments the invention relates to an R-14 polypeptide comprising at least 100, 125, 150, 175, 200, 225, 250, 275, 278, 280, 290, 300, 305, 310, 315, 320 consecutive amino acids of SEQ ID NO:2.

In another aspect, the, invention relates to a recombinant expression system for producing an R-14 protein. For expression in cells, tissues and animals, the nucleic acid as set in SEQ. ID NO. 1 was cloned into a mammalian expression vector, in which R-14 nucleic acid was operably linked to a transcriptional regulatory sequence, e.g., at least one of a transcriptional promoter (for constitutive expression), sequences required for splicing and transcription termination. Such regulatory sequences in conjunction with a R-14 nucleic acid molecule provided a useful vector for gene expression. People skilled in the art could use similar strategies to express R-14 protein in prokaryotic and eukaryotic host cells transfected with appropriate expression vectors in vitro (e.g. cell culture) and in vivo (e.g. transgenic) methods for producing R-14 proteins.

The present invention further pertains to methods of producing the subject R-14 polypeptides. For example, a "host cell" transfected with a nucleic acid "vector" directing expression of a nucleotide sequence encoding the subject polypeptides can be cultured under appropriate conditions to allow expression of the peptide to occur. Suitable media for cell culture are well known in the art. The recombinant R-14 polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptides. In a preferred embodiment, the recombinant R-14 polypeptide is a fusion protein containing a domain which facilitates its purification, such as polyhistidine fusion of R-14 protein.

The invention also provides fusion proteins, e.g., R-14 conjugated to green fluorescent protein or beta arrestin. Such fusion proteins can provide detection of R-14 polypeptides in cells, tissues and organisms. Fusions of green fluorescent protein (GFP) to R-14 protein can be used to locate and follow the dynamics of R-14, such as aggregation, association with other cellular proteins, internalization, trafficking, degradation in endocytotic vesicles, in living or fixed cells. R-14 fusions of GFP and luciferase can be used to study and monitor dimer and oligomer formation, association with other signalling molecules. R-14-$G_\alpha$ protein fusions can be used to measure GTP binding and hydrolysis by the G protein in response to agonists or antagonists and these methods, known to people skilled in the art, are used to screen and/or test small molecule compound libraries for agonist or antagonist activity. These examples are presented to illustrate, but not to limit the potential fusion partners and their uses in basic and applied scientific studies.

Moreover, it will be generally appreciated that, under certain circumstances, it may be advantageous to provide homologs of one of the subject R-14 polypeptides, which function in a limited capacity as one of either an R-14 agonist (mimetic) or an R-14 antagonist, in order to promote or inhibit only a subset of the biological activities of the naturally-occurring form of the protein. Homologs of each of the subject R-14 proteins can be generated by mutagenesis, such as by discrete point mutation(s), or by truncation. For instance, mutation can give rise to homologs which display elevated ligand-independent activity or substantially the same, or merely a subset of the biological activity of the R-14 polypeptide from which it was derived. Alternatively, antagonistic forms of the protein can be generated which are able to inhibit the function of the naturally occurring form of the protein, such as by competitively binding to an R-14 receptor.

R14 Activity and Assaying Said Activity

In one aspect, the invention provides methods for identifying a compound that can modulate R-14 "activity". Such a method may entail determining the activity of an R-14 protein in the presence of a test or candidate compound. Such a method may for, example be used to identify an R-14 antagonist, which may be useful for lowering intraocular pressure, and further for treating a condition associated with elevated intraocular pressure, such as glaucoma and related conditions. Various aspects of R-14 activity may be assayed in this regard, as noted herein and in the Examples.

In an embodiment, determining R-14 "activity" entails assaying an interaction between an R-14 polypeptide and an R-14 binding partner, to identify compounds that are capable of interfering with the interaction of R-14 and its binding partner, and thus the test compound may be capable of binding to an R-14 polypeptide. In an embodiment, such a method includes the steps of (a) forming a mixture, which includes: (i) an R-14 polypeptide, (ii) an R-14 binding partner and (iii) a test compound; and (b) detecting interaction of the R-14 polypeptide and the R-14 binding partner or alteration in at least one aspect of R-14 polypeptide "activity". A statistically significant change (potentiation or inhibition) in R-14 activity in the presence of the test compound, relative to that in the absence of the test compound, indicates a potential agonist or antagonist (inhibitor) respectively of R-14 bioactivity for the test compound. The reaction mixture can be a cell-free protein preparation, e.g., a reconstituted protein mixture or a cell lysate or purified cell constituents, or a cultured cell recombinantly expressing the R-14 polypeptide or fragments thereof. People skilled in the art can use such a competitive binding assay to detect the interaction between an R-14 polypeptide and a, R-14 binding partner. In an embodiment, at least one of the R-14 polypeptide and the R-14 binding partner comprises a detectable label, and interaction of the R-14 and R-14 binding partner is quantified by detecting the label in the complex. The detectable label can be, e.g., a radioisotope, a fluorescent compound, an enzyme, or an enzyme co-factor.

Cell-Free Assays

Cell-free assays can be used to identify compounds which are capable of interacting with an R-14 protein, thereby modify the activity of the R-14 protein. Such a compound can, e.g., modify the structure of, an R-14 protein and thereby affect its activity. Cell-free assays can also be used to identify compounds which modulate the interaction between an R-14 protein and a R-14 binding partner. In a preferred embodiment, cell-free assays for identifying such compounds consist essentially in a reaction mixture containing an R-14 protein, R-14 binding partner and a test compound. A test compound can be, e.g., a derivative of a R-14 polypeptide or R-14 binding partner.

Accordingly, one exemplary screening assay of the present invention includes the steps of (a) forming a reaction mixture including: (i) an R-14 polypeptide, (ii) an R-14 binding partner, and (iii) a test compound; and (b) detecting interaction of the R-14 and the R-14 binding protein. For detection purposes, the binding partner can be labelled with a specific marker such as a radionuclide, or a fluorescent compound or an enzyme. Interaction of a test compound with an R-14 protein or fragment thereof can then be detected by determining the level of the marker label after an incubation step and a washing step. The R-14 polypeptide and R-14 binding partner can be produced recombinantly, purified from a source, e.g., plasma, or chemically synthesized, as described herein. A statistically significant change (potentiation or inhibition) in the interaction of the R-14 and R-14 binding protein in the presence of the test compound, relative to the interaction in the absence of the test compound, indicates a potential agonist (mimetic or potentiator) or antagonist (inhibitor) of R-14 bioactivity for the test compound. Radiolabelled samples are counted and quantified by scintillation spectrophotometry. Binding ligands can be conjugated to enzymes such as acetylcholine esterase and bound R-14-binding partner can be quantified by enzyme assay.

Cell-free assays can also be used to identify compounds which interact with an R-14 protein and modulate an activity of an R-14 protein. Accordingly, in one embodiment, an R-14 protein is contacted with a test compound and the bioactivity of R-14 is monitored. The bioactivity of R-14 protein in cell-free assays include, GTP binding, GTP hydrolysis, Dissociation of $G_□$ proteins, adenylate cyclase activation, phospholipase (A2, beta, gamma and D isoforms) activation, phospholipid hydrolysis, cAMP synthesis etc. and the methods of measuring these changes in the bioactivity of R-14 protein are well known to those skilled in the art.

Cell Based Assays

In addition to cell-free assays, such as described above, R-14 proteins as provided by the present invention, facilitate the generation of cell-based assays, e.g., for identifying an agent capable of modulating R-14 activity, such as small molecule agonists or antagonists. Cell based assays can be used, for example, to identify compounds which modulate the bioactivity of R-14 protein, expression of an R-14 gene or those genes that are induced or suppressed in response to increased or decreased bioactivity of R-14 protein. Accordingly, in one embodiment, a cell which is capable of producing R-14 is incubated with a test compound in the presence or absence of a natural or synthetic agonist/ antagonist of R-14 and the bioactivity of R-14 is measured. The resultant alterations in the bioactivity of R-14 are compared to control R-14 producing cells which have not been contacted with the test compound. These measurements are used to assess the potency, affinity, action of the test compound towards modulating R-14 bioactivity.

A particular embodiment of the present invention is that cell-free and cell-based assays involving the use of R-14 protein as set forth in SEQ ID NO. 2, could become an integral part of a screening system to evaluate and select small molecules which can be optimized to be used as therapeutics for lowering intraocular pressure and in the treatment of glaucoma.

Kits

The invention further provides kits for use in diagnostics or screening methods for providing R-14 binding partners or glaucoma therapeutics. For example, the kit can comprise (1) a labeled R-14 binding partner and/or (2) cell-free lysates or cellular fractions including membranes isolated from R-14 expressing host cells or R-14-expressing tissues or whole cells expressing R-14 protein naturally or by recombinant DNA methods and/or (3) an agent capable of detecting R-14 protein or mRNA and/or (4) means for determining the amount of R-14 protein, mRNA or bioactivity and the means for comparing the amount of R-14 protein, mRNA or bioactivity in the sample with a standard. The compound or agent can be packaged in a suitable container. The kit can further comprise instructions for using the kit to detect R-14 mRNA or protein or its bioactivity. Such a kit can comprise, e.g., one or more nucleic acid probes capable of hybridizing specifically to at least a portion of an R-14 gene or allelic variant thereof, or mutated form thereof.

R14 as a Drug Target in Intraocular Hypertension

Applicants' results described herein indicate that R-14 protein represents a drug target, i.e. with a view to provide R-14 modulators which may be useful for lowering intraocular pressure and thus may be useful for the treatment of conditions associated with elevated intraocular pressure, such as glaucoma and related conditions. In a more preferred embodiment, the invention provides a method by which R-14 gene and protein can be expressed in host cells such as mammalian cells, and the cells be used for small molecule or peptide lead compound discovery in order to provide pharmaceutical compositions useful in treating patients diagnosed with elevated intraocular pressure and related conditions such as glaucoma.

R14 Antagonists, Pharmaceutical Compositions, Uses Thereof

Applicants have further identified and characterized agents (e.g. peptide compounds) capable of modulating R-14 activity, e.g. can act as peptide antagonists of R-14 activity. Accordingly, the invention provides peptide compounds for use in lowering intraocular pressure. In a further embodiment, the invention provides peptide compounds for use in the treatment of a condition associated with elevated intraocular pressure such as glaucoma and related conditions. The invention further provides a method of lowering intraocular pressure in a subject and a method for the treatment of a condition associated with elevated intraocular pressure such as glaucoma and related conditions, the methods comprising administering an effective amount of a peptide/peptide compound of the invention, or a composition comprising a peptide of the invention, to the subject, e.g. a subject in need thereof. In an embodiment, the subject is a mammal, in a further embodiment, a human.

Therefore, in an aspect, the invention provides a substantially pure peptide compound of Formula I:

$$Z_1\text{-}X_1\text{-}X_2\text{-}X_3\text{-}X_4\text{-}X_5\text{-}X_6\text{-}X_7\text{-}X_8\text{-}Z_2 \quad\quad I$$

wherein:

$X_1$ is selected from the group consisting of Phe, His, Ile and related amino acids;

$X_2$ is selected from the group consisting of Ser, Ile, Phe and related amino acids $X_3$ is selected from the group consisting of Leu, Ile, Asp and related amino acids $X_4$ is selected from the group consisting of Thr, Cys, Ser and related amino acids possessing side chains containing sulfhydryl, hydroxyl or H-bond forming groups;

$X_5$ is selected from the group consisting of Gln, Ser, Thr and related amino acids;

$X_6$ is selected from the group consisting of Lys, Pro, Glu and related amino acids;

$X_7$ is selected from the group consisting of Tyr, Leu, Cys and related amino acids;

$X_8$ is selected from the group consisting of Cys, Arg, Trp and related amino acids;

$Z_1$ is an N-terminal group of the formula $H_2N-$, RHN— or, RRN—;

$Z_2$ is a C-terminal group of the formula —C(O)OH, —C(O)R, —C(O)OR, —C(O)NHR, —C(O)NRR;

R at each occurrence is independently selected from $(C_1$–$C_6)$ alkyl, $(C_1$–$C_6)$ alkenyl, $(C_1$–$C_6)$ alkynyl, substituted $(C_1$–$C_6)$ alkyl, substituted $(C_1$–$C_6)$ alkenyl, or substituted $(C_1$–$C_6)$ alkynyl; and "—" is a covalent linkage.

In a further embodiment, $Z_1$ is an N-terminal group selected from the group consisting of a proton, a sequence of 1–3 amino acids, or a blocking group such as a carbamate group, an acyl group composed of a hydrophobic moiety such as cyclohexyl, phenyl, benzyl, short chain linear and branched alkyl groups of 1–8 carbons. In a further embodiment, $Z_2$ is a carboxy-terminal group selected from the group consisting of a proton, $NH_2$, 1–3 amino acids as well as arylalkyl amines such as benzylamine, phenylethylamine, phenylpropylamine, and aliphatic amines possessing short chain linear and branched alkyl groups of 1 to 8 carbons.

The invention further provides a substantially pure synthetic peptide compound or recombinant peptide compound, said compound having a domain of Formula II:

$$-X_1\text{-}X_2\text{-}X_3\text{-}X_4\text{-}X_5\text{-}X_6\text{-}X_7\text{-}X_8\text{-} \quad\quad II$$

wherein $X_1$, $X_2$, $X_3$, $X_4$, $X_5$, $X_6$, $X_7$, $X_8$ and "—" are defined as above.

In embodiments, the peptide compound comprises a sequence selected from the group consisting of:

$NH_2$-Phe Ser Leu Thr Gln Lys Tyr Cys-OH (FSLTQKYC; SEQ ID NO:3);

$NH_2$-His Ile Ile Cys Ser Pro Leu Arg-OH (HIICSPLR; SEQ ID NO:4); and $NH_2$-Ile Phe Asp Ser Thr Gln-Cys Trp-OH (IFDSTECW; SEQ ID NO:5).

The invention further provides an active fragment of the above noted peptides. "Active fragment" refers to a fragment of a peptide of the invention which is capable of modulating the activity of an R-14 protein, wherein said R-14 protein comprises a polypeptide selected from the group consisting of:

(a) the polypeptide of SEQ ID NO. 2; and
(b) a polypeptide encoded by a first nucleic acid that is substantially identical to a second nucleic acid capable of encoding the polypeptide of SEQ ID NO. 2.

The invention further provides derivatives of the above (SEQ ID NOs:3, 4 and 5) which may be synthetic polypeptides containing conservative substitutions of individual amino acids, and peptidomimetics thereof.

The invention further provides a recombinant expression system, vectors and host cells, such as those described above, for the expression/production of a peptide comprising a peptide of the invention (such as those set forth in SEQ ID NOs. 3, 4 and 5), using for example culture media, production, isolation and purification methods such as those described above. Such vectors comprise a nucleic acid sequence capable of encoding such a peptide operably linked to a transcriptional regulatory sequence. In an embodiment, the peptide is a fusion peptide containing a domain which facilitates its purification, such as a polyhistidine domain.

The invention also aims to provide a pharmaceutical composition comprising a peptidic or peptidomimetic compound with a pharmaceutically acceptable carrier, wherein said compound is capable of modulating, in an embodiment inhibiting at least one aspect of R-14 polypeptide bioactivity.

The invention also aims to provide a pharmaceutical composition containing a peptidic or peptidomimetic compound with a pharmaceutically acceptable carrier, wherein said compound is capable of decreasing intraocular pressure.

Also within the scope of the invention are pharmaceutical compositions for treating patients diagnosed with increased intraocular pressure and/or glaucoma, comprising administering (e.g., either locally or systemically) to a subject, a pharmaceutically effective amount of a composition comprising a compound capable of modulating at least one aspect of R-14 bioactivity.

R14 Antagonists, Active Fragments, Peptidomimetics Thereof

The invention also provides for reduction of the fragments of R-14 antagonists to generate mimetics, e.g., peptide or non-peptide agents, such as small molecules, which are agonistic or antagonistic of R-14 protein activity.

In order to improve the R-14 antagonists described in this invention for therapeutic use, several modifications of the peptide can be made by substituting a first amino acid with a "related amino acid" which is a second amino acid related to the first amino acid by either structure or function of the side chain: aromatic, aliphatic, positively- or negatively-charged. Examples of related amino acids are provided in Tables 2 and 3 below.

TABLE 2

Examples of related amino acids

| Residue | Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg |
| Met | Leu; Ile; Val |
| Phe | Met; Leu; Tyr |
| Ser | Thr |
| Thr | Ser |
| Trp | Tyr; His; Phe |
| Tyr | Trp; Phe |
| Val | Ile; Leu |
| Pro | Ala; Gly |

Alternatively, another group of substitutions of the R14 antagonists of the present invention are those in which at least one amino acid residue has been removed and a different residue inserted in its place according to the following Table 2. Another group of substitutions are defined herein as exchanges within one of the following five groups:

TABLE 3

Relations among amino acids

| Small aliphatic, nonpolar or slightly polar residues | Ala, Ser, Thr, (Pro, Gly) |

TABLE 3-continued

Relations among amino acids

| Polar, negatively charged residues and their amides | Asp, Asn, Glu, Gln |
| Polar, positively charged residues | His, Arg, Lys |
| Large aliphatic, nonpolar residues | Met, Leu, Ile, Val, (Cys) |
| Aromatic residues | Phe, Tyr, Trp |

The three amino acid residues in parentheses above have special roles in protein architecture. Gly is the only residue lacking any side chain and thus imparts flexibility to the chain. This however tends to promote the formation of secondary structure other than alpha-helical. Pro, because of its unusual geometry, tightly constrains the chain. It generally tends to promote beta turn-like structures. Cys is capable of participating in disulfide bond formation. Tyr, because of its hydrogen bonding potential, has significant kinship with Ser, and Thr, etc.

In addition, any amino acid representing a component of the said peptides can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Additional variations include b- and g-amino acids that provide different spatial arrangement of chemical groups.

In addition to the substitutions outlined above, synthetic amino acids that provide similar side chain functionality can be introduced in to the peptide. For example, aromatic amino acids may be replaced with D- or L-naphthylalanine, D- or L-Phenylglycine, D- or L-2-thienylalanine, D- or L-1-, 2-, 3- or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines where alkyl may be substituted or unsubstituted methyl, ethyl, propyl, hexyl, butyl, pentyl, isopropyl, iso-butyl, iso-pentyl groups. Non-carboxylate amino acids can be made to possess negative charge, such as the non-limiting examples of phosphono- or sulfated (e.g. $-SO_3H$) amino acids.

Other substitutions may include unnatural alkylated amino acids which are made by combining an alkyl group with any natural amino acid. Basic natural amino acids such as lysine, arginine may be substituted with alkyl groups at $NH_2$. Others are nitrile derivatives (e.g., containing the CN-moiety in place of $CONH_2$) of asparagine or glutamine, and sulfoxide derivative of methionine. In addition, any amide linkage in the peptide can be replaced by a ketomethylene, hydroxyethyl, ethyl/reduced amide, thioamide or reversed amide moieties, e.g. ($-C=O$)$-CH_2-$), ($-CHOH$)$-CH_2-$), ($CH_2-CH_2-$), ($-C=S$)$-NH-$), or ($-NH-$($-C=O$) for ($-C=O$)$-NH-$).

Compounds of the invention can be prepared, for example, by replacing, deleting, or inserting an amino acid residue of a peptide compound or domain of the invention, with other conservative amino acid residues, i.e., residues having similar physical, biological, or chemical properties, and screening for biological function. It is well known in the art that some modifications and changes can be made in the structure of a polypeptide without substantially altering the biological function of that peptide, to obtain a biologically equivalent polypeptide. The peptides, ligands and domains of the present invention also extend to biologically equivalent peptides, ligands and domains that differ from a portion of the sequence of novel ligands of the present invention by conservative amino acid substitutions. As used herein, the term "conserved amino acid substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6)s are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (J. Mol. Bio. 179:125–142, 1984). Genetically encoded hydrophobic amino acids include Gly, Ala, Phe, Val, Leu, Ile, Pro, Met and Trp, and genetically, encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —$NO_2$, —NO, —$NH_2$, —NHR, —NRR, —C(O)R, —C(O)OH, —C(O)OR, —C(O)$NH_2$, —C(O)NHR, —C(O) NRR; etc., where R is independently ($C_1$–$C_6$) alkyl, substituted ($C_1$–$C_6$) alkyl, ($C_1$–$C_6$) alkenyl, substituted ($C_1$–$C_6$) alkenyl, ($C_1$–$C_6$) alkynyl, substituted ($C_1$–$C_6$) alkynyl, ($C_5$–$C_{20}$) aryl, substituted ($C_5$–$C_{20}$) aryl, ($C_6$–$C_{26}$) alkaryl, substituted ($C_6$–$C_{26}$) alkaryl, 5–20 membered heteroaryl, substituted 5–20 membered heteroaryl, 6–26 membered alkheteroaryl or substituted 6–26 membered alkheteroaryl. Genetically encoded aromatic amino acids include Phe, Tyr, and Tryp, while non-genetically encoded aromatic amino acids include phenylglycine, 2-napthylalanine, beta-2-thienylalanine, 1,2,3,4-tetrahydro-isoquinoline-3-carboxylic acid, 4-chlorophenylalanine, 2-fluorophenylalanine3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held, equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3,-diaminopropionic acid, 2,4-diaminobutyric acid, and homoarginine.

The above classifications are not absolute and an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for, free hydroxyl groups or N-im-benzylhistidine for the imidazole nitrogen of histidine. Peptide analogues also include amino acids that have been chemically altered, for example, by methylation, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogues can also include replacement of the amide linkage in the peptide with a substituted amide (for example, groups of the formula —C(O)—NR, where R is ($C_1$–$C_6$) alkyl, ($C_1$–$C_6$) alkenyl, ($C_1$–$C_6$) alkynyl, substituted ($C_1$–$C_6$) alkyl, substituted ($C_1$–$C_6$) alkenyl, or substituted ($C_1$–$C_6$) alkynyl) or isostere of an amide linkage (for example, —$CH_2NH$—, —$CH_2S$, —$CH_2CH_2$—, —CH=CH— (cis and trans), —C(O)$CH_2$—, —CH(OH)$CH_2$—, or —$CH_2SO$—).

In order to improve the pharmaceutical characteristics of the R-14 antagonists, the size of the peptides can be reduced by deleting one or more amino acids and use amino acid mimetics or dipeptide mimics containing non-peptide bonds. Examples of using molecular scaffolds such as benzodiazepine, azepine, substituted gamma lactam rings, keto-methylene pseudopeptides, β-turn dipeptide cores and β-aminoalcohols for these purposes are known to peptide chemists and are described in in *Peptidomimetic protocols* (*Methods in molecular medicine Vol.* 23) W. M. Kazmierski (ed.), Humana Press and *Advances in Amino Acid Mimetics and Peptidomimetics, Vols.* 1 & 2 A. Abell (Ed).

Covalent modifications of the peptide are thus included within the scope of the present invention. Such modifications may be introduced into the R-14 antagonists by reacting targeted amino acid residues of the polypeptide with an organic derivatizing agent that is capable of reacting with selected side chains or terminal residues. The following examples of chemical derivatives are provided by way of illustration and not by way of limitation. Cysteinyl residues may be reacted with alpha-haloacetates (and corresponding amines), such as 2-chloroacetic acid or chloroacetamide, to give carboxymethyl or carboxyamidomethyl derivatives. Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0. Lysinyl and amino terminal residues may be reacted with compounds such as succinic or other carboxylic acid anhydrides. Other suitable reagents for derivatizing alpha-amino-containing residues include compounds such as imidoesters/e.g. as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosinyl residues per se is well-known, such as for introducing spectral labels into tyrosinyl residues by reaction with aromatic diazonium compounds or tetranitromethane. N-acetylimidazol and tetranitromethane may be used to form O-acetyl tyrosinyl species and 3-nitro derivatives, respectively.

Carboxyl side groups (aspartyl or glutamyl) may be selectively modified by reaction with carbodiimides (R'—N=C=N—R') such as 1-cyclohexyl-3-(2-morpholinyl-(4-ethyl)carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions. Glutaminyl and asparaginyl residues may be frequently deamidated to the corresponding glutamyl and aspartyl residues. Other modifications of the peptides in the present invention may include hydroxylation of proline and lysine, phosphorylation of hydroxyl groups of seryl or threonyl residues, methylation of the alpha-amino groups of lysine, arginine, and histidine side chains acetylation of the N-terminal amine, methylation of main chain amide residues (or substitution with N-methyl amino acids) and, in some instances, amidation of the C-terminal carboxyl groups, according to known method steps.

Covalent attachment of fatty acids (C6–C18) to the peptides confer additional biological properties such as protease resistance, plasma protein binding, increased plasma half life, intracellular penetration etc. The above description of modification of a R14 antagonist peptides does not limit the scope of the approaches nor the possible modifications that can be engineered.

Peptides or peptide analogues can be synthesised by standard chemical techniques, for example, by automated synthesis using solution or solid phase synthesis methodology. Automated peptide synthesisers are commercially available and use techniques well known in the art. Peptides and peptide analogues can also be prepared using recombinant DNA technology using standard methods. Accordingly, the invention further provides nucleic acids that encode peptide compounds of the invention. Such nucleic acids may be introduced into cells for expression using standard recombinant techniques for stable or transient expression. Nucleic acid molecules of the invention may include any chain of two or more nucleotides including naturally occurring or non-naturally occurring nucleotides or nucleotide analogues.

Methods of Treatment

The present invention provides for both prophylactic and therapeutic methods of treating a subject having elevated intraocular pressure and/or glaucoma and related conditions. Therefore, the invention further provides a method for lowering intraocular pressure or for treating a condition associated with elevated intraocular pressure, such as glaucoma and related conditions, in a subject, the method comprising administration of an agent which is capable of R-14 antagonist activity. Administration of a prophylactic agent can occur prior to the manifestation of symptoms characteristic of the R-14 aberrancy, such that glaucoma is prevented or, alternatively, its progression delayed. In general, the prophylactic or therapeutic methods comprise administering to the subject an effective amount of a compound which is capable of antagonizing a wildtype R-14 activity or agonizing a mutant (defective) R-14 activity. Examples of suitable compounds include the antagonists, agonists or homologues described in detail herein.

Effective Dose

Toxicity and therapeutic efficacy of agents capable of modulating R-14 activity, such as R-14 agonists or antagonists, can be determined by standard pharmaceutical procedures in experimental animals, e.g., for determining The $LD_{50}$ (The Dose Lethal To 50% Of The Population) and The $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. The dosage of such compounds lies preferably within a range of circulating concentrations that include the $ED_{50}$ with little or no toxicity. The dosage may vary within this range depending upon the dosage form employed and the route of administration utilized. A dose may be formulated in animal models to achieve a circulating plasma concentration range that includes the $IC_{50}$ (i.e., the concentration of the test compound which achieves a half-maximal inhibition of symptoms) determined in in vitro and ex vivo assays and animal studies. Such information can be used to more accurately determine useful doses in humans. Levels of R-14 therapeutics in plasma may be measured, for example, by high performance liquid chromatography. The effective dose of a R-14 therapeutic (agonist or antagonist) could be 0.01 micrograms-100 mg and is determined by the route of administration, pharmaceutical preparation and the mode of delivery.

Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation (either through the mouth or the nose) or oral, buccal, parenteral or rectal administration. Techniques and formulations generally may be found in Remimington's Pharmaceutical Sciences, Meade Publishing Co., Easton, Pa.). For topical administration, R-14 therapeutics of the invention are formulated into solutions, ointments, salves, gels, or creams as generally known in the art. For example, a solution containing a R-14 therapeutic can be applied as drops directly on the eye to lower intraocular pressure.

In one embodiment, such compositions include an agent capable of modulating R-14 activity, such as an R-14 antagonist, in a therapeutically or prophylactically effective amount sufficient to reduce intraocular pressure, and a pharmaceutically acceptable carrier.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the R-14 antagonists can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. R-14 antagonist) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, an R-14 antagonist may be formulated with one or more additional compounds that enhance the solubility of the R-14 antagonist.

A further form of administration is to the eye. An agent or compound capable of modulating R-14 activity, such as an R-14 antagonist, may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye.

A further aspect of the present invention is a method of lowering intraocular pressure in a subject and/or preventing and/or treating a condition associated with elevated intraocular pressure (e.g. glaucoma), by administering to a subject a nucleic acid molecule encoding a peptide compound of the invention. Suitable methods of administration include gene therapy methods.

A nucleic acid of the invention may be delivered to cells in vivo using methods such as direct injection of DNA, receptor-mediated DNA uptake, viral-mediated transfection or non-viral transfection and lipid based transfection, all of which may involve the use of gene therapy vectors. Direct injection has been used to introduce naked DNA into cells in vivo (see e.g., Acsadi et al. (1991) Nature 332:815–818; Wolff et al. (1990) Science 247:1465–1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) J. Biol. Chem. 263:14621; Wilson el al. (1992) J. Biol. Chem. 267:963–967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel el al. (1991) Proc. Natl. Acad. Sci. USA 88:8850; Cristiano et al. (1993) Proc. Natl. Acad. Sci. USA 90:2122–2126).

Defective retroviruses, are well characterized for use as gene therapy vectors (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include .psi.Crip, .psi.Cre, .psi.2 and .psi.Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

For use as a gene therapy vector, the genome of an adenovirus may be manipulated so that it encodes and expresses a peptide compound of the invention, but is inactivated in terms of its ability to replicate in a normal lytic viral life cycle. See for example Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482–6486), hepatocytes (Herz and Gerard (1993) Proc. Natl. Acad. Sci. USA 90:2812–2816) and muscle cells (Quantin el al. (1992) Proc. Natl. Acad. Sci. USA 89:2581–2584).

Adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. Curr. Topics in Micro. and Immunol. (1992) 158:97–129). AAV may be used to integrate DNA into non-dividing cells (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). An AAV vector such as that described in Tratschin et al. (1985) Mol. Cell. Biol. 5:3251–3260 may be used to introduce DNA into cells (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790). Lentiviral gene therapy vectors may also be adapted for use in the invention.

General methods for gene therapy are known in the art. See for example, U.S. Pat. No. 5,399,346 by Anderson et al. A biocompatible capsule for delivering genetic material is described in PCT Publication WO 95/05452 by Baetge et al. Methods of gene transfer into hematopoietic cells have also previously been reported (see Clapp, D. W., et al., Blood 78: 1132–1139 (1991); Anderson, Science 288:627–9 (2000); and Cavazzana-Calvo et al., Science 288:669–72 (2000)).

The invention further relates to transplantation methods, to introduce into a subject a cell comprising a nucleic acid capable of encoding a peptide compound of the invention. The nucleic acid may be present in a vector as described above, the vector being introduced into the cell in vitro, using for example the methods described above. In an embodiment, the cell is autologous, and is obtained from the subject. In embodiments, the cell is allogeneic or xenogeneic.

In embodiments, the therapeutic method may be used in conjunction with a diagnostic method. For example, a subject suffering from a condition associated with intraocular pressure (e.g. glaucoma) may be identified or diagnosed using a diagnostic method and then subsequently treated using a therapeutic method. Further, the therapeutic method may be used for treatment in conjunction with the diagnostic or prognostic method which is used to monitor the progress of the treatment.

In accordance with another aspect of the invention, therapeutic compositions of the present invention, comprising a R-14 antagonist, may be provided in containers or commercial packages which further comprise instructions for use of the R-14 antagonist for the prevention and/or treatment of elevated intraocular pressure and related disorders such as glaucoma.

Accordingly, the invention further provides a commercial package comprising an R-14 antagonist or the above-mentioned composition together with instructions for the prevention and/or treatment of elevated intraocular pressure and related disorders such as glaucoma.

The invention further provides a use of the above-noted peptides, compounds and compositions for lowering intraocular pressure in a subject and/or for the prevention and/or treatment of elevated intraocular pressure and related disorders such as glaucoma.

The invention further provides a use of the above-noted peptides, compounds and compositions for the preparation of a medicament for lowering intraocular pressure in a subject and/or for the prevention and/or treatment of elevated intraocular pressure and related disorders such as glaucoma.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Example 1

Cloning and Characterization of the Nucleic Acid Encoding R-14

In silico analysis of EST # HTM1-025F1 (GenBank Acc.: BE439409) against human genome using BLAST-N (v. 2.2.1) program resulted in a hit of 99.8% similarity to HTM1-025F1 in contig NT_009307.3, AC020568.4 on chromosome 11. A 966 bp fragment was amplified from a BAC clone, RP11–206C1 obtained from the Sanger Center, UK, by PCR, using gene specific primers, 5' GATTCAAC-CATCCCAGTCTTGGGTACAG 3' (SEQ ID NO:6) and 5' TTACTGCTCCAATCTGCTTCCCGACAGC 3' (SEQ ID NO:7). PCR was done using Taq HiFi (Invitrogen, CA) following the protocol suggested by the manufacturer (annealing at 60° C. for 30 sec, elongation at 68° C. for 80 sec: total cycles—35). The PCR products were separated using 1% agarose gels. A photograph of the gel is shown in FIG. 1(A). –Bac: No plasmid DNA; +Bac: contains plasmid DNA (0.1 μg); MW std: λ Hind III digest. The ~960 bp fragment (indicated by arrow) was cloned into pcDNA4HisMax TOPO TA (Invitrogen, CA) according to the manufacturer's instructions. Orientation of the cloned insert was assessed by PCR using vector-specific and gene-specific primers (5' TATGGCTAGCATGACTGGT 3' (SEQ ID NO:8) vector's Express epitope coding sequence and 5' TTACTGCTCCAATCTGCTTCCCGACAGC 3' (SEQ ID NO:7) gene specific 3' end primer). Three clones were sequenced by the dideoxy sequencing method.

The nucleotide sequence of the R-14 reading frame is shown in FIG. 1(B). The sequences obtained from 2 clones were 99.5% homologous to HTMI-0025 (Gonzalez et al., supra) except for a C (instead of an A) at position 626. R14.0 protein sequence was 99.4% homologous to MGRx3, a gene sequence identified during a search of mas-oncogene related sequences in mouse and human genomes (Dong X et al. [2000] Cell. 106:619).

The R-14 polypeptide sequence is shown in FIG. 1(C). The seven underlined sequences show potential hydrophobic transmembrane domains. Shaded residues represent potential phosphorylation sites; PKA (R-X1-2-S/T-X) or PKC (X-S/T-X-R/K).

Example 2

Expression of R-14 mRNA in Human Trabecular Meshwork Tissue

Method: RT-PCR of total mRNA isolated from human trabecular meshwork (HTM) and human iris (HI) tissues. Aliquots of total RNA (1 μg) were reverse transcribed (50° C. for 30 min) and the reaction mixture was amplified for 35 cycles (60° C. for 30 sec) using gene-specific primers SuperScript One-Step RT-PCR (InVitrogen). Resolution of the PCR products by agarose gel electrophoresis showed a single DNA fragment of 1 Kb from HTM tissue, but not from iris tissue. Sequencing of the DNA fragment from HTM tissue identified the 1 Kb fragment to contain the R-14 reading frame.

Example 3

Expression of Cloned Human R-14 Receptor in Human Cells

Cell culture: HEK293 cells were grown in complete DMEM (10% fetal calf serum, 0.1% Penicillin and streptomycin, 2 mM glutamine, 0.5 ug/ml fungizone, 5 ug/ml gentamicin) until ~70% confluent. Cells were transfected using Lipofectamine 2000 (InVitrogen) according to the manufacturer's recommendations using 12.5 μg DNA and 25 μl Lipofectamine in DMEM. Media was replaced after 48 hours for complete DMEM (The cells were processed immediately to detect transient expression of R-14), supplemented with 500 μg/ml Zeocin. After 3 weeks in culture, the zeocin-resistant cells (R14/293) were split and cultured in complete DMEM with 100 μg/ml Zeocin.

Figure 3:
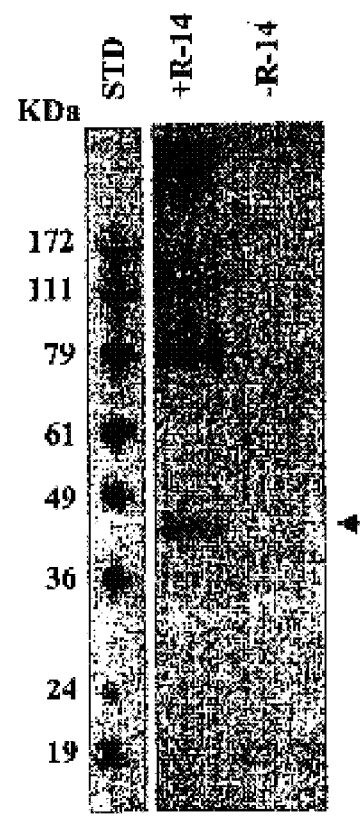
FIG. 3: Immunoblot analysis of expression of cloned human R-14 receptor in human cells as described in Example 3. Arrow shows R-14 immunoreactive band.
Figure 4A:
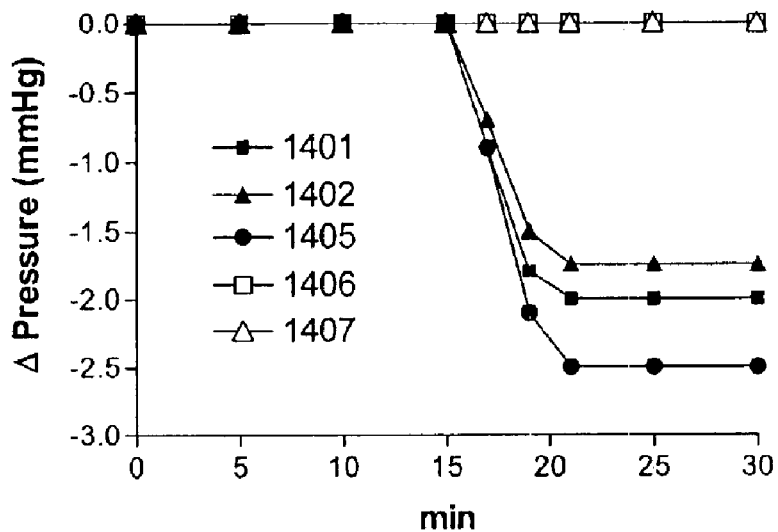
FIG. 4: Graphical results of identification and characterization of inhibitors of R-14 protein as described in Example 4.
Figure 4B:
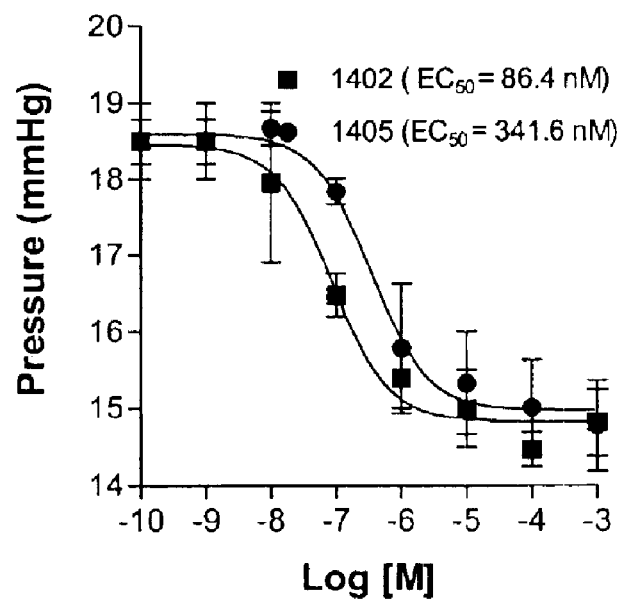
Figure 5:
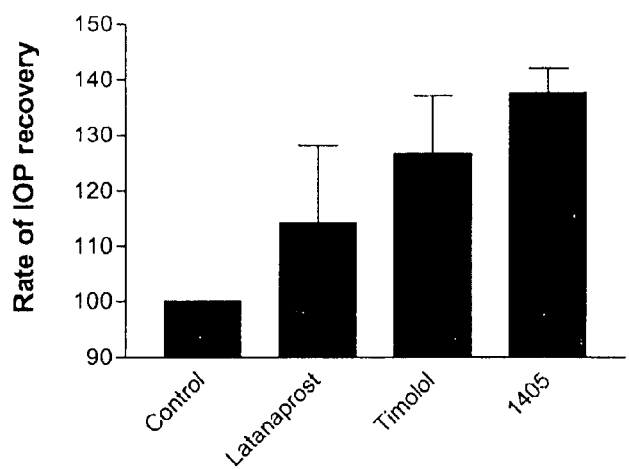
FIG. 5: Graphical results of comparison of the efficacy of peptide 1405 with Latanoprost and Timolol as described in Example 5.

Immunoblotting of R-14 proteins: Confluent cells were lysed in TNE (10 mM Tris-HCl pH 7.4, 0.1 mM EDTA, 0.85% NaCl, 1% NP-40) buffer containing protease inhibitor cocktail. Aliquots (100 μg protein) of supernatants were denatured in 50 μl of SDS-loading buffer by boiling for 5 minutes and resolved on 10% SDS-acrylamide gels. Proteins were transferred to PVDF membrane by electroblotting and was blocked with 5% dry milk BLOTTO for 1 h, and incubated with mouse anti-HIS (1/2000) for 1 h, washed, then incubated with goat anti mouse-HRP (1/2000) in TBST for 1 hour. Membrane was rinsed with TBS and developed by colorimetry using a DAB/CN substrate (Pierce). The details of immunoblotting are given in Moore D et al (Ed) *Current protocols in molecular biology* 1987. John Wiley & sons inc. With reference to FIG. 3, R14+ refer to HEK 293 cells expressing recombinant R14 fusion protein (HIS-tag) whereas R14– refer to parent HEK293 cells which do not contain native R-14 receptor. The immunoreactive R-14 band is indicated by an arrow.

Example 4

Identification and Characterization of Peptide Inhibitors of R-14 Protein

Method: Newborn pigs (1–3 days old) were anesthetized with 1.5% halothane for tracheostomy and catheterization of the right femoral vein for drug administration. Animals were ventilated by means of a Harvard small animal respirator with a gas mixture of 25% 02 and 75% $N_2$. Halothane was discontinued after surgery and immediately thereafter the animals were sedated with Alpha-chloralose (50 mg/kg i.v.) and paralyzed with pancuronium (0.1 mg/kg i.v.). Animals were placed under radiant warmer to keep their body temperature at 37° C. A butterfly needle (24G) is inserted into the anterior chamber of both eyes and connected to a Statham pressure transducer connected to a Gould multichannel recorder. Intraocular pressure is then allowed to stabilize for 15 minutes. Peptides were prepared by standard chemical methods of peptide synthesis. Peptides dissolved in saline were topically applied as drops under the lower eyelid and allowed to diffuse. The intraocular pressure was monitored for 15 minutes at which time a maximal effect was observed.

(A) Effects of peptides on intraocular pressure in piglet. Peptides dissolved in saline were applied to the eye after 15 min of stabilization of intraocular pressure and changes in pressure were monitored for 15 min. The deviation (negative for hypotension) was plotted as a function of time (min). Of the peptides tested, 1401, 1402 and 1405 produced a decrease in ocular pressure within minutes of application, whereas 1406 and 1407 did not affect the basal IOP in the animals.

(B) Dose-response of 1402 and 1405 peptides on intraocular pressure in piglets. The experiments were done as above, except that intraocular pressure was plotted versus the dose of peptide used. Dose response of the peptides on basal IOP of piglet revealed IC50 values of 86.4 and 341.6 nM for 1402 and 1405 respectively.

TABLE 4

Alternative peptides according to embodiments of the invention.

| Peptide | SEQ ID NO: | Sequence | | | | | | | |
|---|---|---|---|---|---|---|---|---|---|
| 1401 | 3 | F | S | L | T | Q | K | Y | C |
| 1402 | 4 | H | I | I | C | S | P | L | R |
| 1405 | 5 | I | F | D | S | T | E | C | W |
| | | $X_1$ | $X_2$ | $X_3$ | $X_4$ | $X_5$ | $X_6$ | $X_7$ | $X_8$ |

Example 5

Comparison of the Efficacy of 1405 with Latanoprost and Timolol

Method: Immediately after euthanasia, rabbit eyeballs were collected and placed into 15-ml organ baths (Radnoti Glass, Monrovia, Calif.). Baths were filled with Krebs (composition in mM: NaCl 120, KCl 4.5, $CaCl_2$ 2.5, $MgSO_4$ 1.0, $NaHCO_3$ 27, $KH_2PO_4$ 1.0, and glucose 10, pH 7.4), maintained at 37° C. and bubbled with 95% 02. The eyeballs were maintained in place with the cornea facing upwards. A butterfly needle (24G) is inserted into the anterior chamber of the eye and connected to a Statham pressure transducer connected to a Gould multichannel recorder. Intraocular pressure is then increased to 35 mmHg manually with saline. The recovery rate (return to 20 mmHg) in the absence (control) or presence of topically applied agents was assessed. Two measurements were averaged, both in the relatively linear portion of the recovery. Control measurements were repeated twice, giving identical results. All values were obtained on the same rabbit eye. Ophthalmic preparations of latanoprost (0.03%) and timolol (0.5%) in addition to peptide 1405 (0.1%) in saline were applied as drops to the eyes. Peptide 1405 reversed experimentally-induced ocular hypertension with an efficiency similar to that of timolol, but significantly faster than latanoprost.

Example 6

Selectivity of Peptides 1402 and 1405

Method: Adult pig eyecup preparations are used to study the response in situ of the relatively undisturbed retinal vasculature. Briefly, a circular incision is made 3–4 mm posterior to the ora serrata to remove the anterior segment and vitreous body with minimal handling of the retina. The remaining eyecup is fixed with pins to a wax base in a 20-ml tissue bath containing Krebs buffer (pH 7.35–7.45) equilibrated with 21% 02 and 5% $CO_2$ and maintained at 37° C. The preparations are allowed to stabilize for 30–45 min, during which they were rinsed two or three times with fresh buffer. Cumulative concentration-response curves to different agents are constructed separately on nonperfused primary arterioles (100–200 µm diameter) of fresh tissue. The outer vessel diameter is recorded with a video camera mounted on a dissecting microscope (model M-400, Zeiss), and responses are quantified by a digital image analyzer (Sigma Scan software, Jandel Scientific, Corte Madera, Calif.). Vascular diameter is recorded before and 10 min after topical application of each concentration of agent, at which time a stable response is generally achieved. Each measurement is repeated three times, and variability is <1%. Additional experiments can be performed after a 20 min pretreatment with a variety of blocking or modulating agents. The responses are expressed as percent change in the outer diameter of vessel from baseline or as a percent reversal of a constrictor agent (Thromboxane receptor agonist, U46619 at a concentration producing a 70% of its maximal effects).

Figure 6:
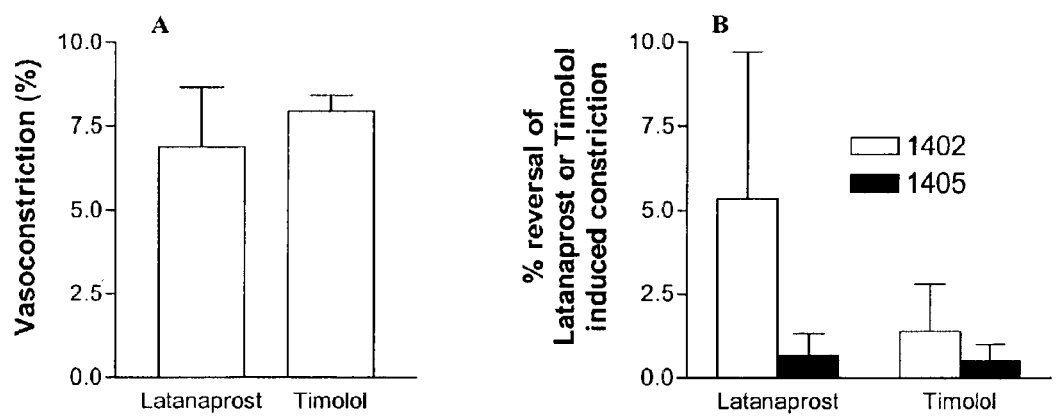
FIG. 6: Graphical results of analysis of selectivity of peptides 1402 and 1405 as described in Example 6.

Both latanoprost and timolol constricted the porcine adult retinal arterioles by an average of 7–8% (FIG. 6A). The R-14 antagonist peptides 1402 and 1405 were tested to measure the relative selectivity of these compounds compared to known ocular hypotensive compounds, latanoprost and timolol. Both 1402 and 1405 peptides did not reverse the constriction produced by latanoprost (by 1–5%) or by timolol (<1%).

Example 7

Effect of Peptides 1402 (A) and 1405 (B) on Intraocular Pressure in Rabbits

Figure 7A:
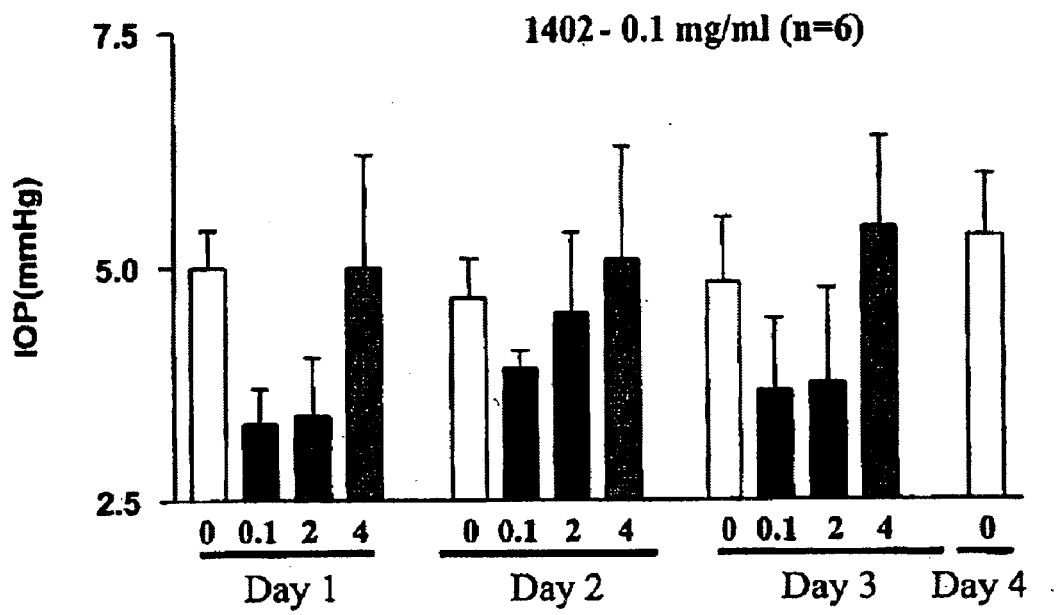
FIG. 7: Graphical results of effect of peptides 1402 (A) and 1405 (B) on intraocular pressure in rabbits, as described in Example 7.
Figure 7B:
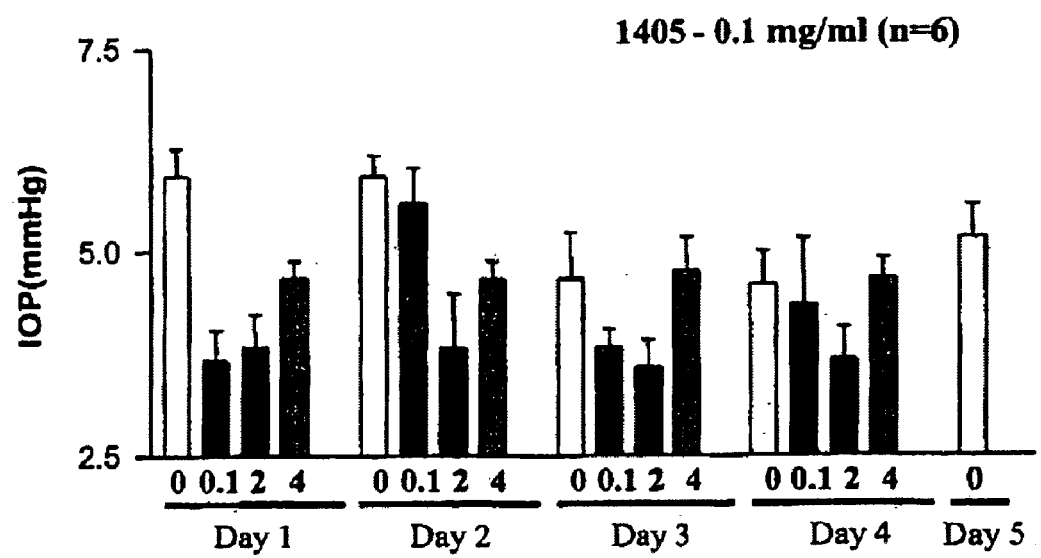

New Zealand white rabbits were trained to stay calm during the application of eye drops and measurement of intraocular pressure (IOP) by flourescein tonometry. Peptides were freshly made in phosphate buffered saline at concentrations indicated and a drop (50 µl) was applied in the irido-corneal angle of the eye. The IOP measurements were taken at different times. As shown in FIG. 7, there was an immediate decrease in IOP by the application of either peptide and the IOP returned to normal values within 4 h. Repeated application of the peptide produced similar decreases in IOP and the effects are reversible with the disappearance of the peptides.

Throughout this application, various references are referred to describe more fully the state of the art to which this invention pertains. The disclosures of these references are hereby incorporated by reference into the present disclosure.

What is claimed is:

1. A substantially pure peptide compound of Formula I:

$$Z_1\text{-Ile-Phe-Asp-Ser-Thr-Glu-Cys-Trp-}Z_2 \quad\quad I$$

wherein:

$Z_1$ is an N-terminal group of the formula $H_2N$—, RHN— or, RRN—;

$Z_2$ is a C-terminal group of the formula —C(O)OH, —C(O)R, —C(O)OR, —C(O)NHR, —C(O)NRR;

R at each occurrence is independently selected from $(C_1-C_6)$ alkyl, $(C_1-C_6)$ alkenyl, $(C_1-C_6)$ alkynyl, substituted $(C_1-C_6)$ alkyl, substituted $(C_1-C_6)$ alkenyl, or substituted $(C_1-C_6)$ alkynyl; and "—" is a covalent linkage.

2. A substantially pure synthetic peptide compound or recombinant peptide compound, said compound having a domain of Formula II:

$$\text{-Ile-Phe-Asp-Ser-Thr-Glu-Cys-Trp-} \quad\quad II$$

wherein

"—" is a covalent linkage.

3. The compound of claim 1, wherein said compound is IFDSTECW (SEQ ID NO: 5).

4. A method of lowering intraocular pressure in a subject, said method comprising administering to said subject an effective amount of the compound of claim 1.

5. A method of treating in a subject a condition associated with elevated intraocular pressure, said method comprising administering to said subject an effective amount of the compound of claim 1.

6. The method of claim 5, wherein the condition is glaucoma.

7. The method of claim 4, wherein said method comprises administering said compound to an eye of said subject.

8. The method of claim 4, wherein the subject is a mammal.

9. The method of claim 8, wherein the subject is human.

10. A pharmaceutical composition comprising the compound of claim 1 in admixture with a pharmaceutically acceptable carrier.

11. The pharmaceutical composition of claim 10, wherein said composition is formulated for administration to an eye of a subject.

12. A package comprising the compound of claim 1 together with instruction for its use.

13. The package of claim 12, wherein said use is selected from the group consisting of:

(a) lowering intraocular pressure in a subject; and (b) treating a condition associated with elevated intraocular pressure.

14. The package of claim 13, wherein said condition is glaucoma.

15. A method of lowering intraocular pressure in a subject, said method comprising administering to said subject an effective amount to the composition of claim 10.

16. A method of treating in a subject a condition associated with elevated intraocular pressure, said method comprising administering to said subject an effective amount of the composition of claim 10.

17. The method of claim 16, wherein the condition is glaucoma.

18. The method of claim 15, wherein said method comprises administering said composition to an eye of said subject.

19. The method of claim 15, wherein the subject is a mammal.

20. The method of claim 19, wherein the subject is human.

21. A package comprising the composition of claim 10, together with instructions for its use.

22. The package of claim 21, wherein said use is selected from the group consisting of:

(a) lowering intraocular pressure in a subject; and (b) treating a condition associated with elevated intraocular pressure.

23. The package of claim 22, wherein said condition is glaucoma.

24. A method of lowering intraocular pressure in a subject, said method comprising administering to said subject an effective amount of the compound of claim 2.

25. A method of treating in a subject a condition associated with elevated intraocular pressure, said method comprising administering to said subject an effective amount of the compound of claim 2.

26. The method of claim 25, wherein the condition is glaucoma.

27. The method of claim 24, wherein said method comprises administering said compound to an eye of said subject.

28. The method of claim 24, wherein the subject in a mammal.

29. The method of claim 28, wherein the subject is human.

* * * * *

SEQUENCE LISTING

<160> NUMBER OF SEQ ID NOS: 8

<210> SEQ ID NO 1
<211> LENGTH: 969
<212> TYPE: DNA
<213> ORGANISM: Homo sapiens
<220> FEATURE:
<221> NAME/KEY: CDS
<222> LOCATION: (1)..(969)
<223> OTHER INFORMATION: coding sequence for polypeptide

<400> SEQUENCE: 1

```
atg gat tca acc atc cca gtc ttg ggt aca gaa ctg aca cca atc aac        48
Met Asp Ser Thr Ile Pro Val Leu Gly Thr Glu Leu Thr Pro Ile Asn
1               5                   10                  15 gga cgt gag gag act cct tgc tac aag cag acc ctg agc ttc acg ggg        96
Gly Arg Glu Glu Thr Pro Cys Tyr Lys Gln Thr Leu Ser Phe Thr Gly
            20                  25                  30 ctg acg tgc atc gtt tcc ctt gtc gcg ctg aca gga gac gcg gtt gtg       144
Leu Thr Cys Ile Val Ser Leu Val Ala Leu Thr Gly Asp Ala Val Val
        35                  40                  45 ctc tgg ctc ctg ggc tgc cgc atg cgc agg aac gct gtc tcc atc tac       192
Leu Trp Leu Leu Gly Cys Arg Met Arg Arg Asn Ala Val Ser Ile Tyr
    50                  55                  60 atc ctc aac ctg gtc gcg gcc gac ttc ctc ttc ctt agc ggc cac att       240
Ile Leu Asn Leu Val Ala Ala Asp Phe Leu Phe Leu Ser Gly His Ile
65                  70                  75                  80 ata tgt tcg ccg tta cgc ctc atc aat atc cgc cat ccc atc tcc aaa       288
Ile Cys Ser Pro Leu Arg Leu Ile Asn Ile Arg His Pro Ile Ser Lys
                85                  90                  95 atc ctc agt cct gtg atg acc ttt ccc tac ttt ata ggc cta agc atg       336
Ile Leu Ser Pro Val Met Thr Phe Pro Tyr Phe Ile Gly Leu Ser Met
            100                 105                 110 ctg agc gcc atc agc acc gag cgc tgc ctg tcc atc ctg tgg ccc atc       384
Leu Ser Ala Ile Ser Thr Glu Arg Cys Leu Ser Ile Leu Trp Pro Ile
        115                 120                 125 tgg tac cac tgc cgc cgc ccc aga tac ctg tca tcg gtc atg tgt gtc       432
Trp Tyr His Cys Arg Arg Pro Arg Tyr Leu Ser Ser Val Met Cys Val
    130                 135                 140 ctc ctc tgg gcc ctg tcc ctg ctg cgg agt atc ctg gag tgg atg ttc       480
Leu Leu Trp Ala Leu Ser Leu Leu Arg Ser Ile Leu Glu Trp Met Phe
145                 150                 155                 160 tgt gac ttc ctg ttt agt ggt gct gat tct gtt tgg tgt gaa acg tca       528
Cys Asp Phe Leu Phe Ser Gly Ala Asp Ser Val Trp Cys Glu Thr Ser
                165                 170                 175 gat ttc att aca atc gcg tgg ctg gtt ttt tta tgt gtg gtt ctc tgt       576
Asp Phe Ile Thr Ile Ala Trp Leu Val Phe Leu Cys Val Val Leu Cys
            180                 185                 190 ggg tcc agc ctg gtc ctg ctg gtc agg att ctc tgt gga tcc cgg aag       624
Gly Ser Ser Leu Val Leu Leu Val Arg Ile Leu Cys Gly Ser Arg Lys
        195                 200                 205 atg ccg ctg acc agg ctg tac gtg acc atc ctc ctc aca gtg ctg gtc       672
Met Pro Leu Thr Arg Leu Tyr Val Thr Ile Leu Leu Thr Val Leu Val
    210                 215                 220 ttc ctc ctc tgt ggc ctg ccc ttt ggc att cag tgg gcc ctg ttt tcc       720
Phe Leu Leu Cys Gly Leu Pro Phe Gly Ile Gln Trp Ala Leu Phe Ser
225                 230                 235                 240 agg atc cac ctg gat tgg aaa gtc tta ttt tgt cat gtg cat cta gtt       768
Arg Ile His Leu Asp Trp Lys Val Leu Phe Cys His Val His Leu Val
                245                 250                 255
```

-continued

```
tcc att ttc ctg tcc gct ctt aac agc agt gcc aac ccc atc att tac      816
Ser Ile Phe Leu Ser Ala Leu Asn Ser Ser Ala Asn Pro Ile Ile Tyr
        260                 265                 270 ttc ttc gtg ggc tcc ttt agg cag cgt caa aat agg cag aac ctg aag      864
Phe Phe Val Gly Ser Phe Arg Gln Arg Gln Asn Arg Gln Asn Leu Lys
            275                 280                 285 ctg gtt ctc cag agg gct ctg cag gac acg cct gag gtg gat gaa ggt      912
Leu Val Leu Gln Arg Ala Leu Gln Asp Thr Pro Glu Val Asp Glu Gly
    290                 295                 300 gga ggg tgg ctt cct cag gaa acc ctg gag ctg tcg gga agc aga ttg      960
Gly Gly Trp Leu Pro Gln Glu Thr Leu Glu Leu Ser Gly Ser Arg Leu
305                 310                 315                 320 gag cag taa                                                          969
Glu Gln
```

<210> SEQ ID NO 2
<211> LENGTH: 322
<212> TYPE: PRT
<213> ORGANISM: Homo sapiens

<400> SEQUENCE: 2

```
Met Asp Ser Thr Ile Pro Val Leu Gly Thr Glu Leu Thr Pro Ile Asn
1               5                   10                  15

Gly Arg Glu Glu Thr Pro Cys Tyr Lys Gln Thr Leu Ser Phe Thr Gly
            20                  25                  30

Leu Thr Cys Ile Val Ser Leu Val Ala Leu Thr Gly Asp Ala Val Val
        35                  40                  45

Leu Trp Leu Leu Gly Cys Arg Met Arg Arg Asn Ala Val Ser Ile Tyr
    50                  55                  60

Ile Leu Asn Leu Val Ala Ala Asp Phe Leu Phe Leu Ser Gly His Ile
65                  70                  75                  80

Ile Cys Ser Pro Leu Arg Leu Ile Asn Ile Arg His Pro Ile Ser Lys
                85                  90                  95

Ile Leu Ser Pro Val Met Thr Phe Pro Tyr Phe Ile Gly Leu Ser Met
            100                 105                 110

Leu Ser Ala Ile Ser Thr Glu Arg Cys Leu Ser Ile Leu Trp Pro Ile
        115                 120                 125

Trp Tyr His Cys Arg Arg Pro Arg Tyr Leu Ser Val Met Cys Val
    130                 135                 140

Leu Leu Trp Ala Leu Ser Leu Leu Arg Ser Ile Leu Glu Trp Met Phe
145                 150                 155                 160

Cys Asp Phe Leu Phe Ser Gly Ala Asp Ser Val Trp Cys Glu Thr Ser
                165                 170                 175

Asp Phe Ile Thr Ile Ala Trp Leu Val Phe Leu Cys Val Val Leu Cys
            180                 185                 190

Gly Ser Ser Leu Val Leu Val Arg Ile Leu Cys Gly Ser Arg Lys
        195                 200                 205

Met Pro Leu Thr Arg Leu Tyr Val Thr Ile Leu Leu Thr Val Leu Val
    210                 215                 220

Phe Leu Leu Cys Gly Leu Pro Phe Gly Ile Gln Trp Ala Leu Phe Ser
225                 230                 235                 240

Arg Ile His Leu Asp Trp Lys Val Leu Phe Cys His Val His Leu Val
                245                 250                 255

Ser Ile Phe Leu Ser Ala Leu Asn Ser Ser Ala Asn Pro Ile Ile Tyr
            260                 265                 270
```

```
Phe Phe Val Gly Ser Phe Arg Gln Arg Gln Asn Arg Gln Asn Leu Lys
            275                 280                 285

Leu Val Leu Gln Arg Ala Leu Gln Asp Thr Pro Glu Val Asp Glu Gly
        290                 295                 300

Gly Gly Trp Leu Pro Gln Glu Thr Leu Glu Leu Ser Gly Ser Arg Leu
305                 310                 315                 320

Glu Gln

<210> SEQ ID NO 3
<211> LENGTH: 8
<212> TYPE: PRT
<213> ORGANISM: Artificial sequence
<220> FEATURE:
<223> OTHER INFORMATION: synthetic peptide

<400> SEQUENCE: 3

Phe Ser Leu Thr Gln Lys Tyr Cys
1               5

<210> SEQ ID NO 4
<211> LENGTH: 8
<212> TYPE: PRT
<213> ORGANISM: Artificial sequence
<220> FEATURE:
<223> OTHER INFORMATION: synthetic peptide

<400> SEQUENCE: 4

His Ile Ile Cys Ser Pro Leu Arg
1               5

<210> SEQ ID NO 5
<211> LENGTH: 8
<212> TYPE: PRT
<213> ORGANISM: Artificial sequence
<220> FEATURE:
<223> OTHER INFORMATION: synthetic peptide

<400> SEQUENCE: 5

Ile Phe Asp Ser Thr Glu Cys Trp
1               5

<210> SEQ ID NO 6
<211> LENGTH: 28
<212> TYPE: DNA
<213> ORGANISM: Artificial sequence
<220> FEATURE:
<223> OTHER INFORMATION: derived from Homo sapiens

<400> SEQUENCE: 6
gattcaacca tcccagtctt gggtacag                                      28

<210> SEQ ID NO 7
<211> LENGTH: 28
<212> TYPE: DNA
<213> ORGANISM: Artificial sequence
<220> FEATURE:
<223> OTHER INFORMATION: derived from Homo sapiens

<400> SEQUENCE: 7
ttactgctcc aatctgcttc ccgacagc                                      28

<210> SEQ ID NO 8
<211> LENGTH: 19
<212> TYPE: DNA
<213> ORGANISM: Artificial sequence
```

```
<220> FEATURE:
<223> OTHER INFORMATION: derived from vector pcDNA4HisMax-TOPO

<400> SEQUENCE: 8
tatggctagc atgactggt                                              19
```